(12) United States Patent
Baez et al.

(10) Patent No.: US 6,511,809 B2
(45) Date of Patent: Jan. 28, 2003

(54) METHOD FOR THE DETECTION OF AN ANALYTE BY MEANS OF A NUCLEIC ACID REPORTER

(75) Inventors: Luis Baez, West Chester, PA (US); Richard C. Ebersole, Newark, DE (US); Edwin R. Hendrickson, Hockessin, DE (US); Neel Neelkantan, Newark, DE (US); Michael P. Perry, Downington, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/858,994

(22) Filed: May 16, 2001

(65) Prior Publication Data

US 2002/0051986 A1 May 2, 2002

Related U.S. Application Data

(60) Provisional application No. 60/211,293, filed on Jun. 13, 2000.

(51) Int. Cl.$^7$ .............................. C12Q 1/68; C12P 19/34
(52) U.S. Cl. ........................ 435/6; 435/91.1; 435/91.2; 435/7.1
(58) Field of Search .................... 435/6, 91.1, 91.2, 435/7.1

(56) References Cited

U.S. PATENT DOCUMENTS

| | | | |
|---|---|---|---|
| 4,668,621 A | | 5/1987 | Doellgast |
| 4,882,269 A | | 11/1989 | Schneider et al. |
| 5,424,413 A | * | 6/1995 | Hogan et al. ............ 536/24.31 |
| 5,648,213 A | * | 7/1997 | Reddy et al. ................... 435/6 |
| 5,665,539 A | | 9/1997 | Sano et al. |
| 5,985,548 A | * | 11/1999 | Collier et al. ................... 435/6 |
| 6,117,631 A | * | 9/2000 | Nilsen ............................ 435/6 |

FOREIGN PATENT DOCUMENTS

WO    WO 93/15229    8/1993

OTHER PUBLICATIONS

D. L. Bates, Trends in Biotechnology, 5(7), 204 (1987).
Vary et al., Clin. Chem., 32, 1696 (1986).
Bobrow et al., J. of Immunol. Methods, 125, 279 (1989).
Bobo et al., Journal of Clinical Microbiol. vol. 28, pp 1968. 1990.
Vogt et al., J. of Immunological Methods, 101, 43 (1987).
Graves, J. of Immunological Methods, 111, 167, (1988).
Wedege et al., J. of Immunological Methods, 88, 233 (1986).
Bodmer et al., J. of Immunoassay, 11, 139, (1990).
Pruslin et al., J. of Immunological Methods, 137, 27, (1991).
Baldo et al., J. of Biochem. and Biophys. Methods, 12, 271, (1986).
Hauri et al., Analytical Biochemistry, 159, 386 (1986).
Rodda et al., Immunological Investigations, 23, 421, (1994).
Tovey et al., Elctrophoresis, 10, 243 (1989).
Kenney et al., Isreal Journal of Medical Sciences, 23, 732, (1987).
Hashida et al., Analytical Letters18, 1143, (1985).
Ruan et al., Ann Clin Biochem, 23, 54, (1985).
WO 89/03891, May 5, 1989, Chiron Corporation, Appl. No. PCT/US88/03644.
European Patent Application No. EO 204 510 A2. Filed May 29, 1986, Amoco Corporation.

* cited by examiner

*Primary Examiner*—Kenneth R. Horlick

(57) ABSTRACT

A process is disclosed for the detection of an analyte utilizing a nucleic acid label as a reporter. The analyte is detected by the binding of at least two reporter conjugates, each conjugate comprising a member of a binding pair and a nucleic acid label. The binding of the reporter conjugates to the analyte facilitates the juxtaposition of the nucleic acid labels, forming a single nucleic acid amplicon. The amplicon may then be detected directly, or may be used as a template of the generation of amplification products. Detection of the analyte by this process significantly reduces assay background caused by non-specific reporter conjugate binding.

26 Claims, 9 Drawing Sheets

METHOD FOR THE DETECTION OF AN ANALYTE BY MEANS OF A NUCLEIC ACID REPORTER

This application claims the benefit of U.S. Provisional Application No. 60/211,293, filed Jun. 13, 2000.

This invention was made with support under CRADA DAMD 17-93-0762 with USAMRIID. Accordingly the United States Government has certain rights in the invention.

FIELD OF THE INVENTION

This invention relates to immunoassays and the use of nucleic acid amplification as a reporting means of the detection of an anlyte. More specifically analyte detection is achieved by forming an analyte dependent reporter-complex (ADRC), joining the reporter labels of the (ADRC), amplifying the joining product of the two labels and detecting the amplification product. Nucleic acid-labels are used to report analyte specific binding. Amplification is achieved by replication of the joined nucleic acid-labels. The method reduces the background signal of a binding assay, thereby, providing means of a highly sensitive analyte detection.

BACKGROUND OF THE INVENTION

The development of immunoassays and advances in methods of nucleic acid amplification have significantly advanced the art of the detection of biological analytes. In spite of these advances, nonspecific binding of the analyte to be detected and general assay noise has remained a problem that has limited the application and sensitivity of such assays. Methods for the reduction of background noise are continually being sought.

The introduction of immunoassays in the 1960's and 1970's greatly increased the number of analytes amenable to precise and accurate measurement. Radio-immunoassays (RIAs) and immunoradiometric (IRMA) assays utilize radioisotopic labeling of either an antibody or a competing analyte to measure an analyte. Detection systems based on enzymes or fluorescent labels were then developed as an alternative to isotopic detection systems. D. L. Bates, *Trends in Biotechnology*, 5(7), 204 (1987), describes one such method based upon enzyme amplification. In this method a secondary enzyme system is coupled to a primary enzyme label. For example, the primary enzyme can be linked catalytically to an additional system such as a substrate cycle or an enzyme cascade. Enzyme amplification results from the coupling of catalytic processes, either by direct modification or by interaction with the product of the controlling enzyme.

U.S. Pat. No. 4,668,621 describes utilization of an enzyme-linked coagulation assay (ELCA) in an amplified immunoassay using a clotting cascade to enhance sensitivity. The process involves clot formation due to thrombin activated fibrin formation from soluble fibrinogen and labeled solubilized fibrinogen. Amplification of the amount of reportable ligand attached to solid-phase is obtained only by combining use of clotting factor conjugates with subsequent coagulation cascade reactions.

Substrate/cofactor cycling is another variation of enzyme-mediated amplification, and is based on the cycling of a cofactor or substrate that is generated by a primary enzyme label. The product of the primary enzyme is a catalytic activator of an amplifier cycle that responds in proportion to the concentration of substrate and hence the concentration of the enzyme label. An example of this type of substrate cycling system is described in U.S. Pat. No. 4,745,054.

Vary et al., *Clin. Chem.*, 32, 1696 (1986) describes an enzyme amplification method suited to nucleic acid detection. This method is a strand displacement assay which uses the unique ability of a polynucleotide to act as a substrate label which can be released by a phosphorylase.

Bobrow et al., *J. of Immunol. Methods*, 125, 279 (1989) discloses a method to improve detection or quantitation of an analyte by catalyzed reporter deposition. Amplification of the detector signal is achieved by activating a conjugate consisting of a detectably labeled substrate specific for the enzyme system, wherein said conjugate then reacts with the analyte-dependent enzyme activation system to form an activated conjugate which deposits wherever receptor for the conjugate is immobilized.

Nucleotide hybridization assays have been developed as a means for detection of specific nucleic acid sequences. U.S. Pat. No. 4,882,269 discloses an amplified nucleic acid hybridization assay in which a target nucleic acid is contacted with a complementary primary probe having a polymeric tail. A plurality of second signal-generating probes capable of binding to the polymeric tail are added to achieve amplified detection of the target nucleic acid. Variations of this methodology are disclosed in PCT Application WO 89/03891 and European Patent Application 204510, which describe hybridization assays in which amplifier or multimer oligonucleotides are hybridized to a single-stranded nucleic acid unit which has been bound to the targeted nucleic acid segment. Signal amplification is accomplished by hybridizing signal-emitting nucleic acid bases to these amplifier and multimer strands. In all of these disclosures amplification is achieved by mechanisms which immobilize additional sites for attachment of signal-emitting probes.

*Journal of Clinical Microbiol.* 28, 1968 (1990) describes a system for detection of amplified *Chlamydia trachomatis* DNA from cervical specimens by fluorometric quantitation in an enzyme immunoassay format which includes a polymerase chain reaction.

U.S. Pat. No. 5,665,539 describes a novel system and method for sensitive analyte detection using immuno-PCR. This consists of a biotinylated DNA which binds to analyte-dependent reporter-complex via a protein A-streptavidin chimeric protein. A segment of the DNA label is amplified by polymerase chain reaction and the products are detected by agarose gel electrophoresis.

In WO 9315229, Applicants disclose a method for the detection of an analyte through the formation of a complex comprising an analyte bound to a reporter having a nucleic acid label attached. Detection of the analyte is effected through amplification of the nucleic acid label.

It is the objective of the art to increase the sensitivity of analyte detection through the use of various novel signal generating reporter conjugates and amplification strategies. However, non-specific binding-signal due to non-selective binding of reporter conjugates to walls of the reaction tubes or to solid-phase reagents used in the assays even in the absence of analyte, is a serious problem in immunoassays. Non-specific binding signal thus diminishes the ratio of the analyte specific binding to analyte non-specific binding. This reduces the sensitivity of the detection limit for an analyte. The art has identified many factors that contribute to non-specific binding such as, protein-protein interaction, adsorptive surface of the solid-phase, Vogt et al., *J. of Immunological Methods*, 101, 43 (1987), the assay milieu and the efficiency of the wash solution.

To resolve this problem a number of approaches have been used in this art by Vogt et al., *J. of Immunological*

Methods, 101, 43 (1987), Graves, *J. of Immunological Methods,* 111, 167, (1988), Wedege et al., *J. of Immunological Methods,* 88, 233, (1986), Bodmer et al., *J. of Immunoassay,* 11, 139, (1990), Pruslin et al., *J. of Immunological Methods,* 137, 27, (1991), Balde et al., *J. of Biochem. and Biophys. Methods,* 12, 271, (1986), Hauri et al., *Analytical Biochemistry,* 159, 386 (1986), Rodda et al., *Immunological Investigations,* 23, 421, (1994), Tovey et al., *Electrophoresis,* 10, 243, (1989), Kenney et al., *Israel Journal Of Medical Sciences,* 23, 732, (1987), Hashida et al., *Analytical Letters,* 18, 1143, (1985), Ruan et al., *Ann Clin Biochem,* 23, 54, (1985). To saturate the adsorptive surface, these investigators have used blocking agents such as, proteins bovine serum albumin (BSA), gelatin, casein, non-fat dry milk, polymers (poly vinyl alcohol) detergents (Tween 20), modified antibodies (Fab' and F(ab')$_2$), and combinations of blocking agents (BSA, Tween 20) and pentane sulfonate. These proteins have been chosen largely by convenience and empirical testing in ELISA systems, Vogt et al., *J. of Immunological Methods,* 101, 43 (1987).

Despite the numerous attempts in this art to use these approaches either individually or in combination, non-specific binding has not been eliminated. Therefore, increased assay detection sensitivity has been limited. Thus, there is a continuing, unmet need for a means to reduce assay background response and to improve the signal to noise ratio of binding assays. The Applicant's invention is the first to apply assay principle that essentially distinguishes between analyte-specific binding reagent recognition and non-specific reagent binding.

SUMMARY OF THE INVENTION

The present invention provides a method for the detection of a specific analyte. In its most basic form the method involves the formation of analyte dependent reporter complex that comprises (i) an analyte and (ii) at least two reporter conjugates bound to the analyte. Each reporter conjugate further comprises a member of a binding pair (such as an antibody) and a nucleic acid fragment or label which is joined to the member of the binding pair. The binding of the both of the reporter conjugates to the analyte operates to bring the nucleic acid labels in close proximity to each other where they may be amplified by means well known in the art. The generation of amplification products is an indication the presence of the analyte. The effect of the instant method is to provide a means of improving the ratio of the analyte-specific signal to analyte non-specific background signal, thus enhancing the ability to detect analytes at very low concentrations.

The invention may be carried out in a variety of formats including a heterogeneous format, a homogeneous format and a multianalyte binding assay format.

The heterogeneous assay format comprises the steps of: a) forming an analyte dependent reporter-complex by equilibrating an analyte to be detected, either simultaneously or in sequence, with a solid-phase analyte capture reagent and at least two reporter conjugates labeled with different nucleic acids; b) forming an analyte specific amplicon (ASA) by selectively joining the nucleic acid-labels of the reporter conjugates bound to the analyte and replicating the ASA); c) forming a nucleic acid product by amplification of the analyte-specific amplicon; d) and detecting the amplified nucleic acid products by sequence and/or size.

The homogeneous assay format will comprise the steps of: a) forming an analyte dependent reporter-complex by equilibrating an analyte to be detected, either simultaneously or in sequence, with at least two reporter conjugates labeled with different nucleic acids; b) forming an analyte-specific amplicon by selectively joining the nucleic acid-labels of the reporter conjugates bound to the analyte and replicating the ASA; c) forming a nucleic acid product by amplification of the analyte specific amplicon; d) and detecting the amplified nucleic acid products by sequence or/and size.

Finally the multianalyte assay format will comprise the steps of: a) forming simultaneously multiple analyte-dependent reporter-complexes by equilibrating analytes to be detected, either simultaneously or in sequence, with solid-phase analyte capture reagent(s) and one set of reporter conjugates for each analyte to be detected; b) forming analyte-specific amplicons by selectively joining the nucleic acid-labels of the reporter conjugates selectively bound to each analyte and replicating the ASA; c) forming nucleic acid products by selective amplification of the analyte-specific amplicons; d) and detecting the amplified nucleic acid products by sequence and/or size.

In conjunction with the above recited formats the present method may effect the amplification of the analyte-specific amplicons in several ways. For example, the amplicon may be formed by the overlap of the nucleic acid labels, or they my be joined enzymatically by means of ligation. Finally, the amplicon may be formed by either method and detected directly, with out amplification by means of signal generating substance.

Thus in one embodiment incorporating ASA formation by nucleic acid overlap, the present invention provides a method for the detection of an analyte comprising: (i) contacting an analyte having at least two reporter conjugate binding sites with at least two reporter conjugates, said reporter conjugates each comprising: a) one member of a binding pair having specificity for at least one reporter conjugate binding site on said analyte; b) a nucleic acid label; wherein said analyte binds to said reporter conjugate forming an analyte dependent reporter complex and wherein said nucleic acid labels on said reporter conjugates are joined by an overlap at each 3' end, forming an analyte specific amplicon; (ii) contacting said analyte specific amplicon with a replication composition wherein said amplicon is amplified forming amplification products; and (iii) detecting said amplification products. Additionally the invention provides that the analyte may be optionally immobilzed prior to complexing with the reporter conjugate(s).

Similarly in an alternate embodiment incorporating amplicon formation by nucleic acid ligation, the present invention provides a method for the detection of an analyte comprising: (i) contacting an analyte having at least two reporter conjugate binding sites with at least one reporter conjugate pair, said reporter conjugate pair comprising a first reporter conjugate and a second reporter conjugate, each of said first and second reported conjugates further comprising: a) one member of a binding pair having an affinity for at least one reporter conjugate biding site on said analyte; b) a nucleic acid label wherein said analyte binds to said reporter conjugate forming an analyte dependent reporter complex and wherein said nucleic acid label of said first reporter conjugate comprises a 3' hydroxyl group and wherein said nucleic acid label of said second reporter conjugate comprises a 5' phosphoryl group and wherein said first and second nucleic acid labels are enzymatically joined to form an analyte specific amplicon; (ii) contacting said analyte specific amplicon with a replication composition wherein said amplicon is amplified forming amplification products; and (iii) detecting said amplification products. This embodiment also provides that the analyte may be optionally immobilzed prior to complexing with the reporter conjugate(s).

In another embodiment the amplicon may be detected directly by a method for the detection of an analyte comprising: (i) contacting an analyte having at least two reporter conjugate binding sites with at least two reporter conjugates, said reporter conjugates each comprising: a) one member of a binding pair having specificity for at least one reporter conjugate binding site on said analyte; b) a nucleic acid label; wherein said analyte binds to said reporter conjugate forming an analyte dependent reporter complex and wherein said nucleic acid labels on said reporter conjugates are joined, forming an analyte specific amplicon; (ii) contacting said analyte specific amplicon with a replication composition comprising a nucleic acid reporting agent, wherein said amplicon is extended and said nucleic acid reporting agent is incorporated into said amplicon; and (iii) detecting said amplicon.

A number of aspects of the present invention are unique as compared to the art. First, two nucleic acid sequences are used as reporter labels. For detection of the analyte, these must be joined together. In this way, joining forms an analyte-specific amplicon whose sequence is unique from that of reporter conjugate labels. The ASA thus functions as a surrogate for the analyte to be detected. Second, three binding-pair reagents are used in contrast to two used by other assays. One binding-pair reagent is for capturing the analyte and two are used for reporter conjugates. Third, the amplification by PCR is used to detect the product of two joined nucleic acid-label in contrast to the amplification product of a single reporter label. Fourth, the random distribution of the non-specifically bound antibodies makes them less likely to be in close proximity to an analyte binding site to interfere with interaction and joining of nucleic acid-labels. Fifth, background is minimized, or is potentially eliminated, improving sensitivity.

The specific binding enables the DNA labels to be in close proximity to each other for coupling of the nucleic acid-labels. The labels can be DNA, RNA, or DNA-RNA hybrid. The PCR amplification product can be detected by various methods known in the art, such as, gel electrophoresis, hybridization of sequence-specific probes or detected indirectly through incorporation of fluorophores, ligands or haptens.

BRIEF DESCRIPTION OF THE FIGURES AND SEQUENCE LISTINGS

Figure 1:
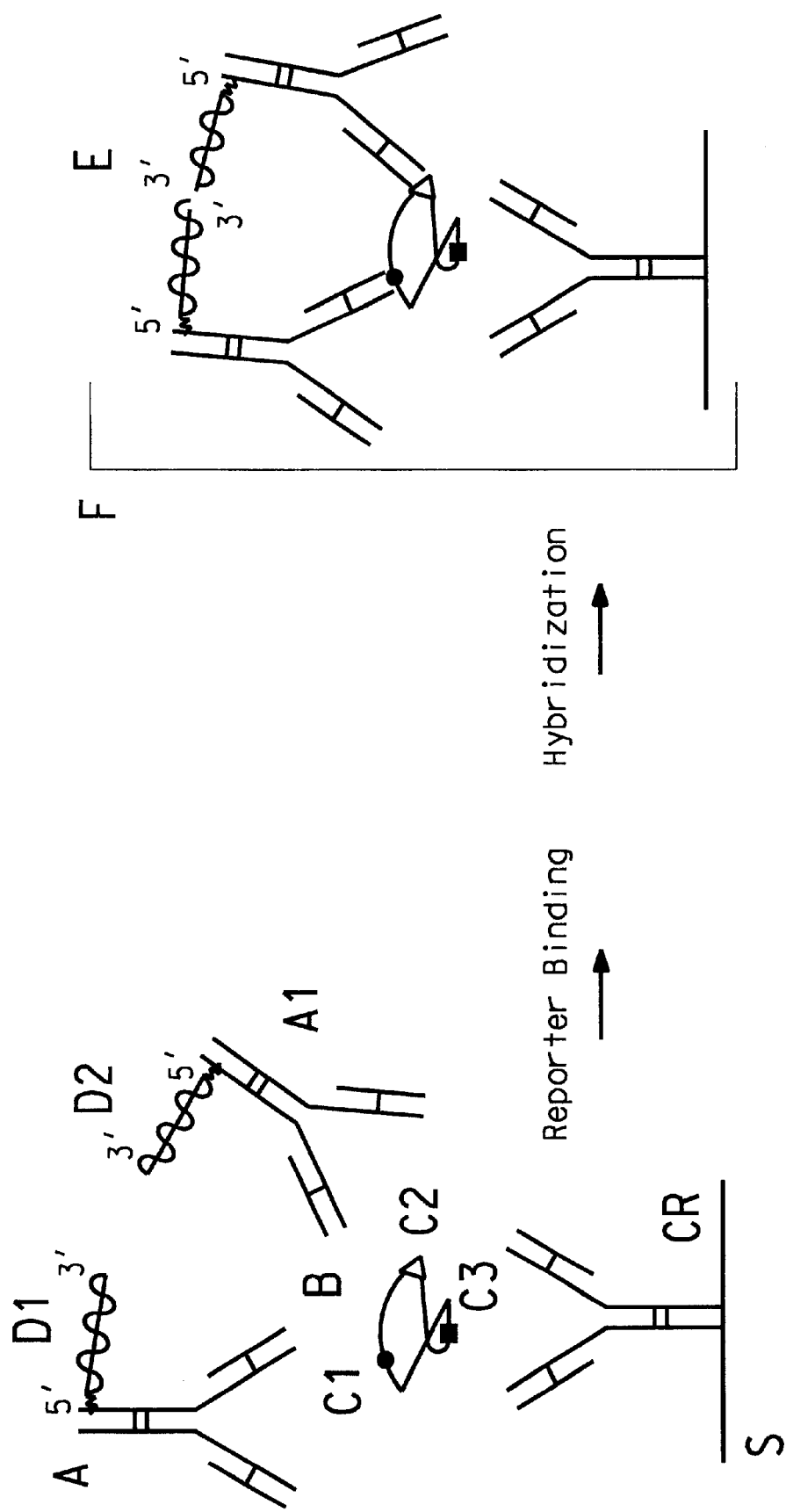
FIG. 1 is a diagram which illustrates the overlap approach for joining the nucleic acid-labels of the analyte bound reporter conjugates to form the analyte-specific-amplicon (ASA) in a heterogeneous format.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the Biochemical Journal 219 (No. 2):345–373 (1984) which are herein incorporated by reference.

SEQ ID NOs: 1–3 correspond to primers used in the examples.

SEQ ID NO:4 is a T78 DNA label used in the ligation format.

SEQ ID NO:5 is a 5' biotinylated T78 DNA label used in the ligation format.

SEQ ID NO:6 is a T68 DNA label used in the ligation format.

SEQ ID NO:7 is a 3' biotinylated T68 DNA label used in the ligation format.

SEQ ID NO:8 is a T68 DNA label used in the overlap format.

SEQ ID NO:9 is a 5' biotinylated T68 DNA label used in the overlap format

SEQ ID NO:10 is a T66 DNA label used in the overlap format.

SEQ ID NO:11 is a 5' biotinylated T66 DNA label used in the overlap format.

SEQ ID NOs:12 and 13 are 3' terminated ligation linkers used in the ligation format.

DETAILED DESCRIPTION OF THE INVENTION

The present invention recites a sensitive method for detecting an analyte by forming an analyte-dependent reporter-complex, joining the reporter labels and amplifying the detectable response of the complex. Nucleic acid-labels are used to report analyte specific binding. Amplification is achieved using replication of the joined nucleic acid-labels.

The present method may be used in a wide variety of applications including the detection of clinical, industrial, agricultural and environmentally important analytes. The invention may be used in both manual, as well as, automated modes. Analytes may be molecules, nucleic acid segments, cells, microorganisms and fragments and products thereof, or any substance for which attachment sites, binding members or receptors (such as antibodies) can be developed. Of particular interest are pathogens, viruses and bacteria. The sample material will most likely be of medical, veterinary, environmental, nutritional or industrial significance including body fluids, such as urine, blood, serum, plasma, milk, sputum, fecal matter, lung aspirates, exudates; microbial culture fluids; aerosols; crop materials; soils and ground waters.

In the context of this disclosure, a number of terms shall be utilized for the interpretation of the claims and the specification.

The term "analyte" refers to a substance to be detected or assayed by the method of the present invention. Typical analytes may include, but are not limited to proteins, peptides, nucleic acid segments, molecules, cells, microorganisms and fragments and products thereof, or any substance for which attachment sites, binding members or receptors (such as antibodies) can be developed.

The term "binding-pair" includes any of the class of immune-type binding-pairs, such as, antigen/antibody or hapten/anti-hapten systems; and also any of the class of nonimmune-type binding-pairs, such as biotin/avidin, biotin/streptavidin, folic acid/folate binding protein or vitamin B12/intrinsic factor. They also include complementary nucleic acid segments (including DNA sequences and peptide nucleic acid sequences), as well as protein A or G immunoglobulins. Binding pairs may also include members that form covalent bonds, such as, sulfhydryl reactive groups including maleimides and haloacetyl derivatives, and amine reactive groups such as isotriocyanates, succinimidyl esters and sulfonyl halides.

The terms "immunoreactive antibody fragment" or "immunoreactive fragment" refer to fragments which contain the binding region of the antibody (Fab or F(ab')$_2$).

The term "label" refers to any atom or molecule that can be attached to a nucleic acid, protein or a member of a binding-pair. A label may be coupled to binding-pair or nucleic acid through a chemically reactive group. A label may be attached to an oligonucleotide during chemical synthesis or incorporated on a labeled nucleotide during nucleic acid replication. Labels specifically designed to report the presence of nucleic acids will be referred to herein as "nucleic acid reporting labels" and will include but are not limited to fluorescent moieties, chemiluminescent moieties, particles, enzymes, radioactive tags, light emitting moieties or molecules and intercalating dyes including propidium iodide (PI) and ethidium bromide (EB) and the cyanine dyes [see for example, U.S. Pat. No. 5,563,037].

The term "reporter" refers to any atom or molecule that is be used as a "label" to provide a detectable (preferably quantifiable) signal, and which can be attached to a nucleic acid, protein or a member of a binding-pair. Reporters may provide signals detectable by fluorescence, luminescence, radioactivity, calorimetric, X-ray diffraction or absorption, magnetism, enzymatic activity, and the like.

The term "nucleic acid-label" refers to a nucleic acid that is used as a "label" to act as a "reporter" and is linked to a member of a binding pair forming a "reporter conjugate". The "nucleic acid-label" may be single-stranded or double-stranded.

The term "reporter conjugate" refers to a conjugate comprising a "nucleic acid-label" coupled to one member of a binding-pair such as an antibody, lectin, receptor or binding protein or other moiety which can bind to an analyte.

The term "reporter conjugate binding site" refers to a specific site on the analyte to which the reporter conjugate will bind. Where, for example, the reporter conjugate comprises an antibody, the reporter conjugate binding site is the antibody epitope on the analyte to be detected.

The term "analyte-specific reporter response" refers to a signal that results from the specific interaction between reporter conjugates and their analytes.

The term "oligonucleotide" refers polydeoxyribonucleotides (containing 2-deoxy-D-ribose), to polyribonucleotides (containing D-ribose) and to any polynucleotide which is an N-glycoside of a purine or pyrimidine base, or modified purine or pyrimidine base. There is no intended distinction between the length of a "nucleic acid", "polynucleotide" or an "oligonucleotide".

The term "primer" is used generally to mean any sequence-binding oligonucleotide which functions to initiate the nucleic acid "replication" process or "amplification" process.

The term "replication" refers to the process in which a complementary strand of a nucleic acid strand of the nucleic acid molecule is synthesized by a polymerase enzyme. In a "primer-directed" replication, this process requires a hydroxyl group (OH) at 3' position of (deoxy)ribose moiety of the terminal nucleotide of a duplexed "primer" to initiate replication.

The term "amplification" refers to the process in which "replication" is repeated in cyclic process such that the number of copies of the nucleic acid sequence is increased in either a linear or logarithmic fashion. Such replication processes may include but are not limited to, for example, Polymerase Chain Reaction (PCR), Ligase Chain Reaction (LCR) Strand Displacement Amplification (SDA) or other such enzymatic reactions.

The term "complementary strand" refers to a nucleic acid sequence strand which, when aligned with the nucleic acid sequence of the one strand of the target nucleic acid such that the 5' end of the sequence is paired with the 3' end of the other sequence, is in antiparallel association, forming a stable duplex. Complementarity need not be perfect. Stable duplexes may be formed with mismatched nucleotides.

The term "enzyme composition" refers to a composition comprising the enzymes necessary to join the DNA labels that make up the reporter conjugate. Where the overlap format is employed, the enzyme composition will contain, at a minimum, a DNA polymerase, along with such other buffers and reagents that will facilitate the ASA formation. Where the ligation format is employed the enzyme composition will contain at a minimum a suitable ligase enzyme similarly along with such other buffers and reagents that will facilitate the ASA formation.

The term "nucleic acid replication composition" or "replication composition" refers to a composition comprising the ingredients necessary for performing nucleic acid replication. Applicants contemplate that replication may be accomplished by any of several schemes known in this art, including but not limited to the polymerase chain reaction (PCR); or the ligase chain reaction (LCR). If PCR methodology is selected, the replication composition would include for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis et al.) and U.S. Pat. No. 4,683,195 (1986, Mullis et al.), which are hereby incorporated by reference. If LCR methodology is selected, then the nucleic acid replication compositions would comprise, for example, a thermostable ligase, e.g., *T. aquaticus* ligase, two sets of adjacent oligonucleotides wherein one member of each set is complementary to each of the target strands, Tris HCl buffer, KCl, EDTA, AND, dithiothreitol and salmon sperm DNA. See, for example, Tabor, S. and Richardson, C. C. (1985) *Proc. Acad. Sci.* USA 82, 1074–1078).

The term "replication inhibitor moiety" refers to any atom, molecule or chemical group that is attached to the 3' terminal hydroxyl group of an oligonucleotide that will block the initiation of chain extension (replication of a strand). Examples include but are not limited to, dideoxynucleotides, 3-deoxy-nucleotides (e.g., cordycepin), phosphate, ligands (e.g., biotin, dinitrophenol), reporters molecules (e.g., fluorescein, rhodamine), carbon chains (e.g., propanol) or a mismatch nucleotide or polynucleotide.

The term "non-participatory" will refer to the lack of participation of a probe or primer in a reaction for the amplification of a nucleic acid molecule. Specifically a non-participatory oligonucleotide is probe, primer or linker which has its 3' hydroxyl group blocked with "replication inhibitor moiety" and will not serve as a substrate for, or be extended by, a DNA or RNA polymerase.

The term "capture reagent" refers to any reagent immobilized on a appropriate support that is capable of reacting with or binding the test analyte(s). "Capture reagents" are typically members of immunoreactive or affinity reactive members of binding-pairs. Where the analyte is immobilized through the action of a capture reagent the resulting complex is referred to as an "analyte-capture-complex".

The term "analyte-dependent reporter-complex" (ADRC) refers to the complex formed by the specific binding of at least two reporter conjugates to the assay analyte in such away that the nucleic acid-labels can be joined to form the "analyte-specific amplicon".

The term "analyte-specific amplicon" (ASA) refers to the nucleic acid product formed by the joining the two assay nucleic acid-labels by either the label-overlap primer approach or the label-ligation approach due to the formation of the analyte-dependent reporter-complex.

The term "nucleic acid amplification product" or "amplification product" refers to the "analyte-specific reporter response" in the context of the present invention, and is the nucleic acid produced by amplification of either the entirety or a portion of the analyte-specific amplicon.

The term "specific binding" or "specific-analyte binding" refers to affinity of a binding-pair reagent(s) limited to an analyte.

The term "non-analyte bound reporter" refers to a reporter conjugate that is not bound to an analyte(s) and is capable of generating an assay signal. This is represented in two forms: (a) in a heterogeneous assay, "non-specific reporter binding"; and (b) in a homogenous assay, "non-specific reporter joining".

In a heterogeneous assay, the term "non-specific binding" or "non-specific reporter binding" refers non-specific affinity of reporter conjugates to the solid-phases of an assay in the absence of analyte. In the context of the present invention, the non-specific affinity of the reporter conjugates that results in a signal, which is produced when the two "nucleic acid-labels" of the present invention are joined, while using the methods of the present invention in the absence of analyte to form the "analyte-specific amplicon".

In a homogenous assay, the term "non-specific joining" or "non-specific reporter joining" refers non-specific joining together of the two "nucleic acid-labels" of the present invention using the methods of the present invention in the absence of analyte to form the "analyte-specific amplicon". The term "overlap" refers to the annealing of the 3" ends of the two proximal positioned DNA labels bound to antibodies to form an overlapped duplex. Once formed, both 3' OH ends of the overlapped duplex serve as primers for a nucleic acid polymerase extension reaction.

The term "overlap format" refers to the assay process that results in the amplification of the "analyte-specific amplicon" formed from the annealing and extension of the 3' ends of the two proximal positioned DNA labels making up the reporter conjugate. The strict conditions for the formation of the overlap are referred to as assay "stringency".

The term "stringency" refers to the strict control of the parameters the affect the stability or the formation of a nucleic acid duplex. This can be temperature(Tm), cation concentrations ($[Na^+]$, $[K^+]$, $[Mg^{2+}]$), the composition and number of nucleotides in the duplex or the concentration of a duplex destabilizing agents (formamide).

The term "ligase" refers to an enzyme that catalyzes the formation of a phosphodiester bond between adjacent 3' hydroxyl and 5' phosphoryl termini of oligonucleotides that are hydrogen bonded to a complementary strand and the reaction is termed "ligation".

The term "ligation" refers to joining of 3' and 5' ends of two proximal positioned antibody bound DNA labels by the enzyme ligase in the presence of a "ligation linker".

The term "ligation linker" is an oligonucleotide that has the complementary strand hydrogen bonded to two oligonucleotides such that it is holding the 3' hydroxyl group of one oligonucleotide in adjacent position to the 5' phosphorylated terminus of the a second oligonucleotide so that a ligase can catalyze the formation of a phosphodiester bond between the two oligonucleotides. The "ligation linker" may be made "non-participatory" where it may be present in an amplification reaction.

The term "ligation format" refers to the assay process that results in the amplification of the "analyte-specific amplicon" formed by the of the joined 3' and 5' ends of two proximal positioned antibodies bound DNA labels by the enzyme ligase in the presence of a "ligation linker".

Standard recombinant DNA and molecular cloning techniques used here are well known in the art and are described by Sambrook, J., Fritsch, E. F. and Maniatis, T., *Molecular Cloning: A Laboratory Manual,* Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions,* Cold Spring Harbor Laboratory Cold Press Spring Harbor, N.Y. (1984); and by Ausubel, F. M. et al., *Current Protocols in Molecular Biology,* published by Greene Publishing Assoc. and Wiley-Interscience (1987).

The present invention proceeds in four stages. First there is binding of the analyte and the reporter conjugate and the formation of the analyte-dependent reporter complex. Optionally, the analyte may be immobilized on a solid support through the action of a capture reagent. Second is the formation of an analyte-specific amplicon (ASA). Next the ASA is amplified generating amplification products, and finally the amplification products are detected.

In one embodiment, the capture reagent, which could be antibody or other members of a binding pair, is bound to the solid-phase such as microtiter plate or polystyrene beads, either passively or covalently. Addition of analyte will enable the formation of the analyte-capture reagent complex. Next, two other antibody-DNA reporter conjugates are added, enabling the formation of the analyte-dependent reporter-complex. This second complex is essential bringing the nucleic acid-labels in close proximity to allow for their coupling, which results in the formation of assay analyte-specific amplicon (ASA). The coupling procedure used will depend on which format is selected in the design of the labels, the overlap format or the ligation format. Each format has its own set of unique reporter DNA labels. Once formed, the ASA is amplified and the amplified product is detected.

Detection Principle

The present invention relates to a novel means of generating a signal for a binding assay that enables the skilled person to distinguishing between an analyte-specific reporter response and a non-specific reporter response. This approach can be used to reduce the background of binding assays and to improve the ratio of the analyte specific signal to analyte non-specific signal. This greatly enhances the ability of the assay to detect analytes at low concentrations.

FIG. 1 more clearly illustrates the basic method, depicting a heterogeneous assay format and the formation of the ASA by nucleic acid label overlap. The invention makes use of nucleic acid-labeled reporter conjugates (A and A1) which selectively bind to the analyte (B). The analyte is comprised of at least two binding sites and possibly more, shown here as C1-C3. The analyte may be immobilized on a solid support (S) through the interaction of the analyte and a capture reagent (CR), typically an antibody. During the assay, the reporter conjugates (A and A1) bind to these binding sites forming ananlyte-dependent-reorter-complex (F). As a consequence, the nucleic acid-labels (D1 and D2) of the bound reporter conjugates are positioned and maintained in close molecular proximity. The spatial proximity being close enough to enable the labels to be joined. For example, the binding of two or more reporter conjugates to the same analyte provides the necessary spatial alignment to enable the nucleic acid-labels to be joined enzymatically to form an analyte-specific amplicon (E). In the formation of the analyte-specific amplicon, the labels are joined as a single nucleic acid molecule. The analyte-specific amplicon is comprised of sequence elements from both nucleic acid-labels. The analyte-specific amplicon thus functions as a molecular surrogate for the analyte. Once joined, the analyte-specific amplicon can then be amplified using appropriate primers and polymerase enzyme.

In contrast, when the reporter conjugates (A and A1) are not bound to the analyte, the reporter conjugates remain free in solution or are non-specifically bound to the surfaces of the solid-phase of the assay. In these instances, the reporter molecules are randomly distributed throughout the reaction solution volume or over the solid-phase area. In either case, the reporter labels are not appropriately aligned or are positioned at distances too great to enable their joining. Consequently, an analyte specific amplicon is not formed. Thus non-analyte bound reporter fraction is either not detected or detected at greatly diminished efficiency.

Figure 2:
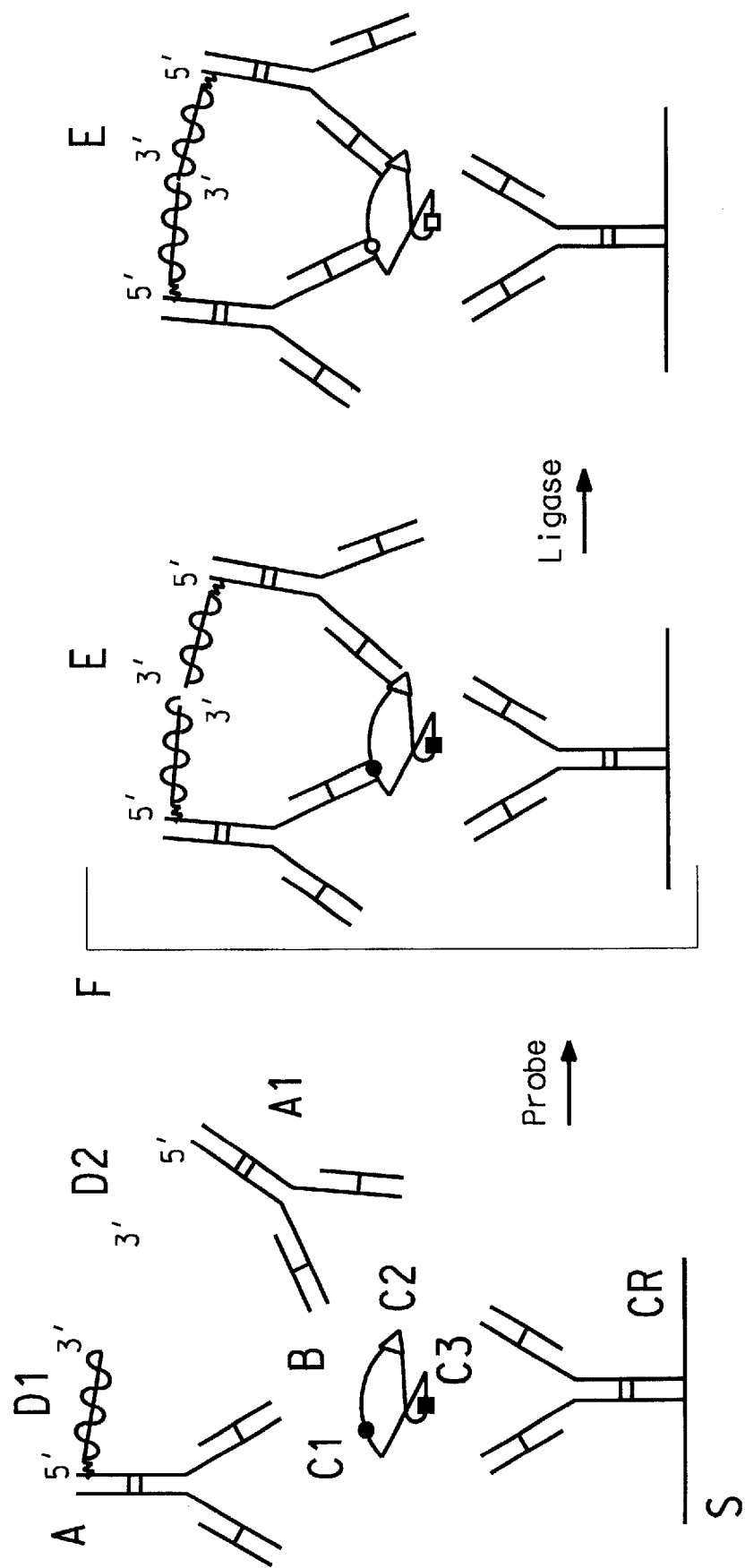
FIG. 2 is a diagram which illustrates the ligation approach for joining the nucleic acid-labels of the analyte bound reporter conjugates to form the analyte-specific-amplicon (ASA) in a heterogeneous format.

Similarly, the ASA may be formed by nucleic acid ligation as illustrated in FIG. 2. The ligation method of ASA formation proceeds essentially as with the overlap method, except that the nucleic acid labels are joined by a ligase prior to amplification.

Both the ligation and overlap methods may be conducted in either a heterogeneous format where the analyte is immobilized, of in a homogeneous format where the analyte is free in solution. It should be noted that, the present method, either in overlap of ligation format has an important advantage over the art in that the nucleic acid-labels can be designed to produce amplification products that can be differentiated on the basis of size of sequence.

For example, the labels can be designed to facilitate replication and amplification of the analyte specific amplicons but not amplification of the individual nucleic acid-labels. This is accomplished by designing primers to anneal to and amplify the analyte-specific amplicon, not to amplify the labels themselves. By this means qualitatively different products are produced in response to the presence or absence of the analyte. Further, the amount of amplification product is directly proportional to the quantity of analyte present. The assay principle thus provides means for both qualitative and quantitative analyte detection.

The basic elements and procedures of the Applicant's invention, such as forming an analyte-dependent reporter-complex, joining the reporter labels and amplifying the analyte-specific amplicon, can be modified and accomplished in different ways. These modifications provide for both new analytical capabilities and increased ease of use.

Assay Configurations

Detection of the analyte may be acomplished in either a heterogeneous or homogeneous assay format. Additionally, a multiplicity of analytes may be detected in the same assay sytem using a multianalyte binding assay.

Heterogeneous Assay Format

In the heterogeneous assay format, the analyte-dependent reporter-complex (ADRC) is comprised of an analyte to be detected, a solid-phase capture reagent, and at least two reporter conjugates. The ADRC is formed in a process in which the analyte, to be detected, is bound to a solid support and the reporter conjugates are bound to the same analyte molecule via separate binding sites on the captured analyte. An immobilized capture reagent on the solid-phase support can be used to augment the selectivity and affinity of capturing the analyte. The ADRC formation can be accomplished in a single step in which the solid-phase reagent, analyte, and reporter conjugates are simultaneously equilibrated together and then washed free of excess, unbound, reporter conjugate. Alternatively, the ADRC complex can be formed in a series of steps in which the analyte and reporter conjugates are sequentially equilibrated with the solid support. Following reagent equilibrations, wash steps can be used to remove excess reporter conjugates.

Once formed, the analyte-dependent reporter-complex is detected by first forming an analyte-specific amplicon. This is accomplished by joining the nucleic acid-labels of the analyte-dependent reporter-complex. This joining process is accomplished enzymatically using ligase or nucleic acid polymerase enzymes. During this process, only those labels which meet the required criteria for both type and spatial alignment are joined. In this way, labels bound to analyte form the ASA, whereas, labels non-attached to the analyte do not form the ASA.

Following formation of the analyte specific amplicon, the amplicon can be detected directly or replicated enzymatically to produce a detectable nucleic acid product. During amplification, the amount of the nucleic acid product can be greatly increased. In this way, the sensitivity of detection is enhanced.

During the assay, both the type of analyte-specific amplicon formed and the amount of the nucleic acid amplification product produced are characteristic of the analyte and proportional to the amount of analyte present. In this way, analytes can be specifically detected and quantified.

Homogeneous Assay Format

In the homogeneous assay format, the analyte-dependent reporter-complex comprises the analyte to be detected, and at least two reporter conjugates. The ADRC is formed in a process in which the analyte is equilibrated with the reporter conjugates. During this process, the analyte-dependent reporter-complex is assembled through binding each reporter conjugate to separate sites on analyte. Typically, this is accomplished in a single step in which the analyte and reporter conjugates are simultaneously equilibrated together and the reaction carried out homogeneously, in solution, without the need for a solid-phase capture reagent.

Once formed, the analyte-dependent reporter-complex is detected by first forming an analyte-specific amplicon. This is accomplished by joining the nucleic acid reporter labels of the analyte-dependent reporter-complex using either of the label joining formats as described for the heterogeneous assay format. During this process, only those labels which meet the required criteria for both type and spatial alignment are joined. The labels of the reporter conjugates remaining free in solution and unattached to the analyte are not joined. In this way, labels bound to analyte form ASA, whereas labels unattached to analyte do not form the ASA. Following its formation the analyte-specific amplicon can be detected directly or amplified enzymatically to produced a detectable nucleic acid product.

Within the homogeneous assay, both the type of analyte-specific amplicon formed and the amount of the nucleic acid amplification product produced are characteristic of the analyte and proportional to the amount of analyte present. In this way, analytes can specifically detected and quantified.

Multianalyte Assay Format

In another preferred embodiment, multiple analytes can be detected simultaneously in the same assay milieu. This is accomplished by using multiple sets of reporter conjugates, each specific for a separate analyte. By slight modifications, multianalyte detection can be accomplished in both a heterogeneous and homogeneous assay formats. For example, a solid-phase containing multiple specific capture reagents could be used in conjugation with multiple sets of reporter conjugates, label-joining and analyte-specific amplicon amplification reagents to accomplish a multianalyte assay. Alternatively, multiple solid-phase reagents, each specific for a separate analyte, could also be employed.

Analytes

The invention may be used to detect a wide variety of analytes. It is a requirement, however, that the analytes contain at least two reporter conjugate binding sites. In this way, at least two reporter molecules can bind to the same analyte. The binding sites of the analyte can be the same or different. Analytes with distinctly different binding sites provide for a greater degree of assay specificity.

Within these requirements, an analyte can be a single molecule, molecular complex, an organism or virus containing multiple reagent binding sites. Since the length of the nucleic acid-labels can be constructed to span varying molecular distances, reagent binding sites need not be on the same molecule. However, they may be on separate, but closely positioned, molecules. For example, the multiple binding epitopes of an organism, such as a virus, bacteria or cell can be targeted by the Applicants' detection methods.

Formation of the Analyte Specific Amplicon

The length of the nucleic acid-labels can be constructed to span varying molecular distances between analyte binding sites. Thus, the reporter conjugate binding sites need not be on the same molecule but may be located on separate, but closely positioned, molecules within a molecular complex or within an organism. For example, microorganisms, such as viruses and bacteria, could be detected by utilizing the repetitive binding epitopes of the organisms and employing DNA labels which span between organism binding epitopes.

A further advantage of the invention is that the distance between the analyte binding sites need not be precisely known to construct an assay for an analyte. Un-hybridized nucleic acid labels are flexible. The rotational freedom of the reporter conjugates are further enabled by the flexibility imparted through both the analyte binding member and the molecular spacers which link the labels to the binding members. Thus reporter conjugate nucleic acid labels in different locations and in different configurations are free to interact through molecular motion and can be detected through formation of analyte specific amplicons. In this way, analyte binding sites in different locations on the analyte can be utilized.

To detect analytes with binding sites at different molecular distances, the reporter conjugates can be prepared with different length nucleic acid labels. For example, a family of reporter conjugates can be prepared each containing the same analyte binding members but different length nucleic acid labels. A workable label length for the analyte can be empirically and readily determined, simply by equilibrating the analyte, in succession, with this family of reporter conjugates, and determining if analyte specific amplicons are formed. In this fashion a workable label length for the analyte can be empirically and readily determined. Thus, the distance between the analyte binding sites need not be known to construct an assay for an analyte.

Reporter conjugates can be prepared with nucleic acid labels ranging in length from 25 bases to 1000 bases, where from about 10 to 200 bases is preferred. Considering the length of both labels, the molecular spacer units and the length of a binding members, (e.g. antibodies), the labels could bridge distances between analyte binding sites as much as a 1000 angstrom or more. Labels, thus, could be designed to bridge the entire length of most viruses or bridge sparsely populated binding sites on cells and microorganism cell surfaces. In conclusion, the flexibility to vary the length of the nucleic acid labels can enable the Applicants' invention to be used for detection of a wide range of analytes.

Joining Enzymes

The joining enzymes used in the assay are dictated by the type of nucleic acid-labels used with reporter conjugate. The overlap format will require the use of labels that form a 3' overlap duplex. This format uses any nucleic acid polymerase that is capable extending 3' OH termini to polymerize a complementary strand to join the two labels and form the ASA. Any polymerase enzyme capable of extending the DNA labels is suitable in the present invention where thermostable DNA polymerases are preferred and Taq polymerase (available from Perkin Elmer-Cetus) is most preferred.

The ligation format will require a ligase enzyme that will catalyze the formation of a phosphodiester bond between 3' hydroxyl and 5' phosphoryl termini of adjacent oligonucleotide-labels, which are a hydrogen bonded to the ligation linker. The ligation reaction joins the two labels to form the ASA. Any ligase enzyme capable of joining the DNA labels is suitable in the present invention. Nucleic acid ligase are well known in the art and suitable ligases may be found in Maniatis, supra.

Capture Reagent Where the invention employs the heterogeneous format it will be necessary to immobilize the analyte for detection. Immobilization is effected through a capture reagent. The capture reagent of the present invention will comprise any material capable of interacting with both the analyte and a solid support. Capture reagents will generally be members of immunoreactive or affinity reactive members of binding-pairs and are generally comprised of, for example, a binding protein, lectin, nucleic acid or an antibody, attached to an appropriate support. Any known antibody could serve as the antibody of the immobilized capture reagent. In certain instances an analyte may serve as the capture reagent by being absorbed directly by nonspecific interaction with the support, as in, for example, the hydrophobic interactions between proteins and polystyrene.

Solid-phase supports to which capture reagents may be affixed are common and well known in the art. A variety of possible supports are contemplated. For example suitable immobilization supports include but are not limited to synthetic polymer supports, such as polystyrene, polypropylene, polyglycidylmethacrylate, substituted polystyrene (e.g., aminated or carboxylated polystyrene; polyacrylamides; polyamides; polyvinylchlorides, etc.); glass, agarose, nitrocellulose, and nylon. These materials may be used as films, microtiter plate, wells, beads, slides, particles, pins, pegs, test tubes, membranes or biosensor chips. Alternatively, the supports could comprise magnetic and non-magnetic particles. Methods for the attachment of binding molecules on solid supports are well known to those skilled in the art and reviewed by H. Weetall, *Immobilized Enzymes, Antigens, Antibodies and Peptides,* (1975) Marcell Dekker, Inc., New York.

Binding-pair Reagents

Specific binding-pair reagents are employed in the assay to capture and report the presence of analyte. The binding-pair agents which can be used as a capture reagent can be of the immune or non-immune type. Immune-specific binding-pairs(analyte inclusive) are exemplified by antigen/antibody systems or hapten/anti-hapten systems. The capture antibody member of a binding-pair, whether it is a polyclonal, a monoclonal or an immunoreactive fragment thereof, of the binding-pair, can be produced by customary methods familiar to those skilled in the art. Immunoreactive antibody fragment or immunoreactive fragment may be Fab-type fragments which are defined as fragments devoid of the Fc portion, e.g., Fab, Fab' and F(ab')$_2$ fragments, or may be "half-molecule" fragments obtained by reductive cleavage of the disulfide bonds connecting the heavy chain components of the intact antibody. If the analyte member of the specific binding-pair is not immunogenic, e.g., a hapten, it can be covalently coupled to a carrier protein to render it immunogenic.

For immune binding members, conventional monoclonal and polyclonal antibodies are of use and represent a preferred immune type binding members. Established methods of antibody preparation therefore can be employed for preparation of the immune type binding reagents. Suitable methods of antibody preparation and purification for the immune type binding member are described Harlow, Ed and Lane, D in *Antibodies A Laboratory Manual,* Cold Spring Harbor Laboratory Press, Cold Spring Harbor, N.Y. (1988).

Non-immune binding-pairs include systems, wherein, the two components share a natural affinity for each other, but are not antigen/antibody-like pairs. Exemplary non-immune binding-pairs are biotin/avidin or biotin/streptavidin, folic acid-folate binding protein, vitamin B12/intrinsic factor, complementary probe nucleic acids, Proteins A, G, immunoglobulins/, etc. Also included are non-immune binding-pairs that form a covalent bond with each other.

The single antibody (binding-pair) approach can be used in a homogeneous or heterogeneous assay format. In a homogeneous format, a single antibody (one member of the binding-pair) can be used when there are two or more binding sites for the antibody on the test analyte. The antibody can then be used to make two different reporter conjugates, each with a different nucleic acid-label.

In a heterogeneous format, a single antibody (one member of the binding-pair) can be used when there are three or more binding sites for the antibody on the test analyte. One site is needed to capture the analyte, and at least two other sites are needed to bind the reporter conjugates. The antibody again is used to make two different reporter conjugates, each with a different nucleic acid-label.

In a preferred embodiment different antibodies are used which recognize different epitopes and thus provide greater specificity to assay. In this embodiment one antibody will serve as capture and the other two antibodies as the reporter conjugates, each with a different label.

It is contemplated that a system employing three monoclonal antibodies that are specific for three different epitopes will give the most sensitive results and is thus most preferred. However, one can use one or two monoclonal and a polyclonal. Immunoreactive fragments like Fab or F(ab')$_2$ can also be used. However, the antibodies should be either affinity purified or through other specific adsorbent columns such as protein A. One could also use non-antibody protein receptors or non-protein receptors such as polynucleic acid aptimers. Polynucleic acid aptimers are typically RNA oligonucleotides which may act to selectively bind proteins, much in the same manner as a receptor or antibody (Conrad et al., *Methods Enzymol.* (1996), 267(Combinatorial Chemistry), 336–367). Theses aptimers will be suitable in the present invention as capture reagents and reporter conjugates.

Amplification of Analyte Bound DNA Antibody Labels

Polymerase chain reaction (PCR) is the preferred method of amplification. Polymerase chain reaction is enzymatic reaction that allows for the amplification of analyte-specific amplicon through repetitive replication process. During each cycle of denaturation, annealing and chain extension, the amplicon sequence is being copied (replicated), i.e., theoretically being doubled. Multiple cycles will result in a logarithmic amplification of the amplicon (e.g., one billion fold for 30 cycles). Therefore, high analyte sensitivity will result from the amplification of the ASA that is formed due to the analyte-dependent reporter-complex. Linear amplification may result from non-specific binding of the reporter conjugates, which results in very little or no formation of the ASA.

PCR of the ASA is typically carried out under conditions well known in the art (see for example Maniatis, supra). The following conditions are exemplary. The amplification mixture will contain a 10 mM Tris-Cl with a pH of 8.3, KCl in a concentration range of 20–60 mM, preferably 50 mM, MgCl$_2$ at 0.5–3 mM, preferably 1.5 mM, 200 $\mu$M DATP, 200 $\mu$M dCTP, 200 $\mu$M dGTP, 200 $\mu$M dTTP, two oligonucleotide primers (50–250 pmol/primer) and 25 units/mL Taq DNA polymerase. PCR is carried out in Template™ Tamers (Coy Corporation, Grass Lake, Mich.) to prevent contamination by the DNA labels or reporter conjugate, which would generate false signals. PCR mixture is added to the wells of PCR microtiter plate (total volume 50 $\mu$L) and 20 $\mu$L of liquid wax (Chill-Out™, MJ Research, Inc., Watertown, Mass.) is layered over the amplification reaction mixture. PCR is performed using an automated thermal cycler (Perkin-Elmer 9600 Thermal cycler). The following temperature profile may be used.

| | |
|---|---|
| Initial label overlap formation and overlap extension: | –25° C. for 3 minutes |
| Polishing extension: | –72° C. for 2 minutes |
| PCR amplification; 30 cycles: | |
| Denaturation | –94° C. for 10 seconds |
| Primer annealing | –54° C. for 15 seconds |
| Extension | –72° C. for 10 seconds. |

After the PCR amplification, each reaction mixture is analyzed for the ASA amplified product by standard agarose gel electrophoresis or through other means as discussed.

Detection of Nucleic Acid Products

The detection of the ASA amplified product may be accomplished by several means including (a) direct detection of the duplex nucleic acids using intercalating dyes; (b) indirect or direct detection of ligands, isotopes or reporters incorporated in the nucleic acids; (c) hybridization of reporter probes to the amplified nucleic acids; or (d) direct detection of replicated product following separation of replicated product from reaction milieu based on increased size of replication product.

Specifically, amplified nucleic acids (the ASA amplified product) can be detected in the reaction mixture by adding intercalating dyes. Of particular use are those dyes of the ethidium, phenazines, furocomarins, phenothiasines and quinoline type which on intercalation with the duplex strands of nucleic acids change dye detection properties. General reviews and further information can be obtained in Berman et al., *Ann. Rev. Biophys. Bioeng,* 20, 87 (1981). For example, a preferred dye is ethidium bromide, which when intercalated into a duplexed-nucleic acid can be detected by excitation of the reaction mixture with short-wave UV light (259–350 nm).

Incorporation of modified nucleotides or modified primers during nucleic acid replication provides a means of introducing nucleotides or oligonucleotides (primers) modified with ligands, isotopes, or reporters. During amplification, these modified bases or primers are incorporated into the amplified product sequences. These approaches afford several detection strategies. For example, the incorporation of biotinylated or ligand modified bases provides means of isolating the amplified nucleic acid products from solution onto a immobilized streptavidin or avidin. The addition of an avidin-signal-generating conjugate then facilitates detection. The amplified sequences may also contain signal-generating labeled bases, such as, fluorescein or digoxigenin. These can be detected directly on the solid-phase support.

In another embodiment, the sequence of the amplified ASA product could be designed to position fluorescent bases within the signal nucleic acids for energy transfer or position the biotinylated bases so that binding of avidin-labeled enzyme(s) reporters would result in enzyme channeling. Using these approaches, the amplified ASA can be detected without the need for separation from the unincorporated bases. According to molecular modeling and recent reports, (R. A. Cardullo et al., *Proc. Natl. Acad. Sci. USA,* 85, 8790 (1988)), energy transfer can be achieved at distances between the fluorophores of as much as 12 bases apart. However, optimum distance appears to be somewhere between 5 to 12 bases. At one fluorophore base per helix turn (10 nucleotides), this positions the donor and acceptor fluorophores in appropriate proximity for energy transfer.

It is contemplated that the analyte-specific amplicon may also be detected directly without nucleic acid amplification. This can be accomplished in a number of ways. Within the context of the ligation approach, the double-stranded region, (comprised of the annealed ASA and linker), can be detected through labeled antibodies specific for double-stranded DNA. The ASA can also be detected through the linker oligonucleotide itself. The linker, for example, may be engineered to contain a label such as biotin or fluorescein. Once the linker is specifically bound to the ASA, the labels could be detected through antibody conjugates, direct fluorescence, or fluorescent energy transfer (FET), for example.

Within the context of the overlap approach, the double-stranded region formed by the overlap of the two nucleic acid labels can be detected through labeled antibodies specific for double-stranded DNA. The ASA may also be detected by FET where the nucleic acid labels contain flourophores that, when in close proximity to each other, change their spectral emission properties. For example, one of the nucleic acid labels may be engineered to contain fluorophore "A" at or near its 3' end while the other would contain fluorophore "B", each fluorophore having its own emission spectrum. When the overlap of the two nucleic acids forms, the fluorophores will be brought into close proximity and a shift in the emission spectrum of one or both fluorophores would be detected. In an alternate embodiment for the detection of the ADRC without nucleic acid amplification may include an extension of the labels in the presence of a labeled nucleotide. For example, once the overlap has formed, the 3' ends would be extended by DNA polymerase I in the presence of the four nucleotides, one of which would be labeled (i.e., biotin or fluorescein, for example). The labeled ASA would then be detected by any number of detection strategies.

Primers and Oligonucleotide Labels

Design of Primers

The primers were designed with the aid of Oligo™ 4.0 (National Biosciences Inc., Plymouth, Minn.). Primers were designed with random base sequences that exhibit specificity, G+C content (around 50%), defined duplex stability (Tm, 52° C.) and duplex internal stability for PCR primers as described by Rychlik et al., *Nucleic Acids Research,* 18, 6401, 1990, *Methods in Molecular Biology,* 15, 31, 1993. Primers were designed to be free of duplex formation (dimers or hairpins), and to have sequences lacking stretches of homopolymers. Further, the primers were designed so that the sequences, comprising the ten 3' terminal bases of each primer, are unique to the primer-binding sites of the DNA label sequence design and are not found in the sequences of either the labels or their complements.

Design of Nucleic Acid-labels

The present assay method uses nucleic acid-labels designs whose structures depend on which of the two assay formats is being used to link the two nucleic acid-labels to form the analyte-specific amplicon (ASA), the overlap format or the ligation format.

The nucleic acid-labels for both approaches use two different labels, each conjugated to the two assay antibodies, which when linked together form the ASA. Each nucleic acid-label was designed to be free of duplex formations (dimers, 3' duplexes or hairpins), and sequences that lack stretches of homopolymers. Each was designed with three defined sequence regions: a 5' sequence, the 3' sequence and a variable "stuffer" sequence between the defined-terminal sequences. The size and functional feature of the 5' and 3' defined-terminal sequences depend on the needs of the format of the assay, overlap or ligation formats. Each nucleic acid-label is designed to be associated with one amplification primer-binding site of the ASA. The primer-binding sites were designed so that their sequences are comprised of the complement to the ten most 3' terminal bases (sequence) of the ASA primer (5' terminal sequence of the primer-binding site) associated with that specific nucleic acid-label. This sequence exists only within the primer-binding sites of that nucleic acid-label or its complement sequence, depending on which format of nucleic acid-labels are being used. Also, these 5' terminal sequence of the primer-binding sites are not found elsewhere in the sequences of either nucleic acid-labels or their complement sequences.

Features of Overlap Labels

Figure 3:
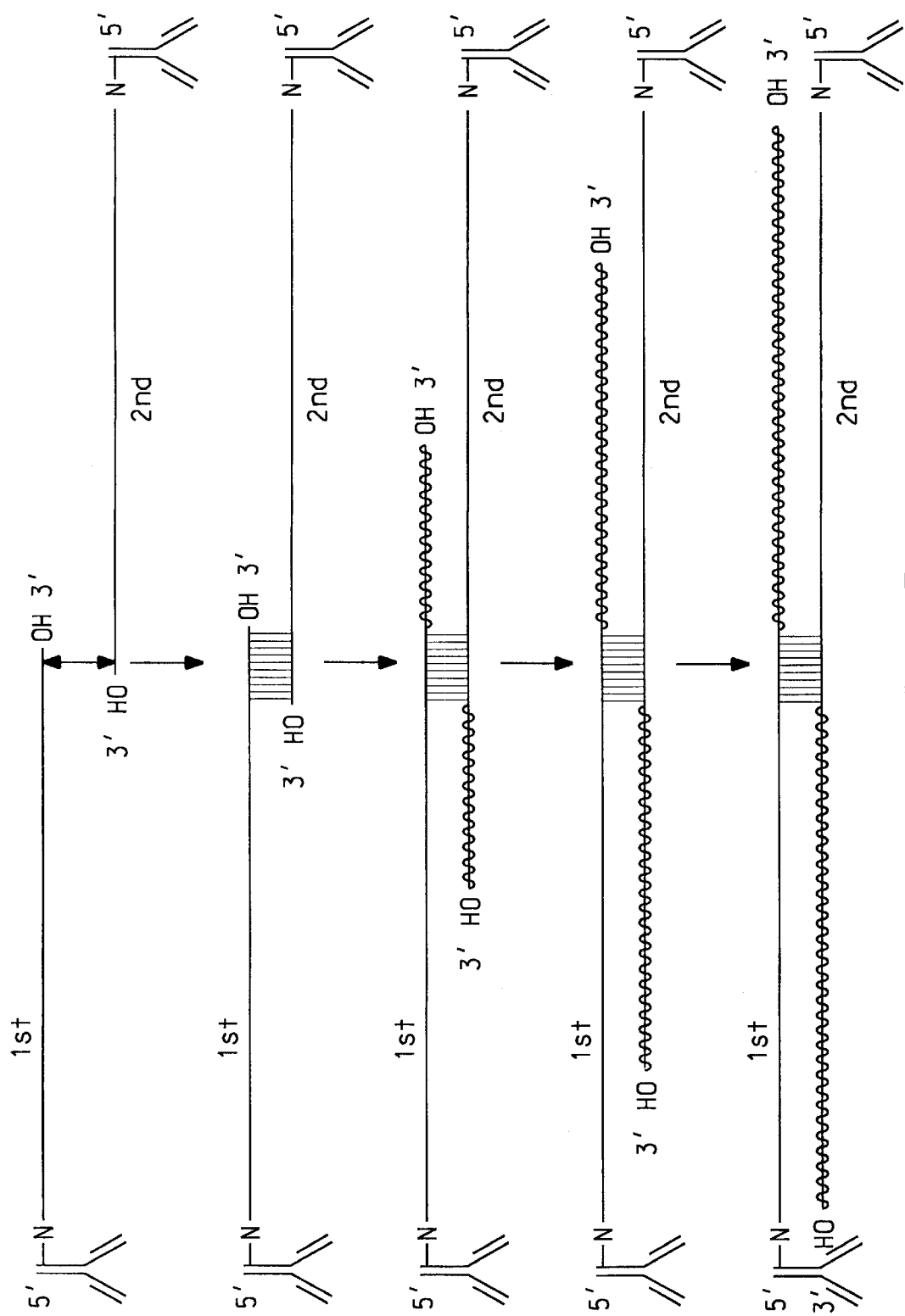
FIG. 3 is a diagram which illustrates the formation of the ASA by DNA labels in the overlap approach.

The nucleic acid-labels for the overlap format consist of two single-stranded oligonucleotides, which are similar in structure. In the overlap format, each nucleic acid-label has a chemically active group (such as, primary amine group) at its 5' end, which allows it to be conjugated to one of two reporter conjugates, each of which must bind to different binding site on the analyte. The 3' end of the first nucleic acid-label (either nucleic acid-label can be the first) is designed to overlap and anneal to the 3' end of the second nucleic acid-label. The overlapped 3' duplex is the essential element of the nucleic acid-label design used in this format. The two analyte-bound nucleic acid-labeled reporter conjugates must be in close proximity to one another (bound to same analyte) to form the 3' duplexed overlap, consisting of the 3' OH ends of both nucleic acid-labels, as shown in FIG. 3. The minimum length of each nucleic acid-label should be long enough to enable the formation this overlapped duplex. Once formed, both 3' OH ends of the overlapped duplex serve as primers for a nucleic acid polymerase extension reaction. Each 3' OH end can be extended by the nucleic acid polymerase to form the double-stranded ASA, which consists of the overlapped nucleic acid-labels from both reporter conjugates and their newly formed chain-extended complement.

The nucleotide composition of the overlap regions influences the temperature range at which the formation of a stable overlapped duplex occurs. An important criterion for the design of the nucleic acid-labels is that the nucleotide composition of the overlap region on each label will allow for the formation of a stable duplex at temperatures that enables the chain-extension of the 3' overlapped nucleic acid-labels by a nucleic acid polymerase. This results in the synthesis of the complementary strands and formation of the double-stranded ASA. At the same time, the base composition of the overlapped region must also be designed to meet the criteria that prohibit the formation of a stable 3'-duplex at temperatures where the reporter conjugates are being bound to analyte and where post-binding wash steps occur. In addition the duplex should not be stable in the range of temperatures at which the ASA is being amplified. If the duplex is stable at any or all of these assay-restricted temperatures, an 3' duplex could be formed between a nucleic acid-label of one reporter conjugate, which is bound non-specifically to solid-phase of the assay format, and another reporter conjugate, which is in solution. The duplexed overlap could then be chain-extended, the ASA be formed and then amplified, thus giving the assay a false positive signal.

The stringency of the formation of the duplex can be further controlled by adjusting the cation concentration or the concentration of a helix destabilizing agents. Such conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein. For Duplex formation it will be necessary that Hybridization the two nucleic lables contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

Features of Ligation Labels

Figure 4:
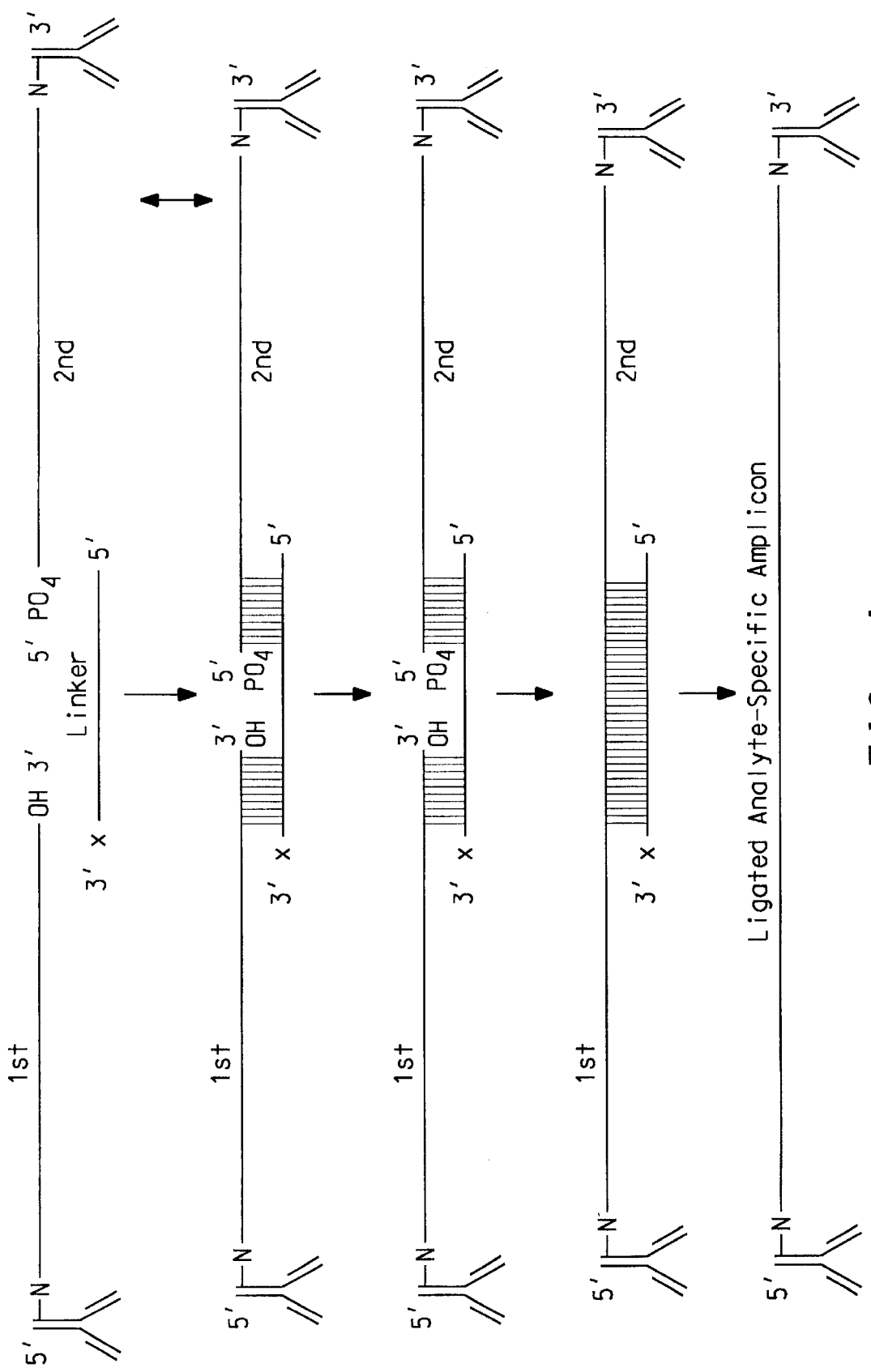
FIG. 4 is a diagram which illustrates the formation of the ASA by DNA labels in the ligation approach.

The nucleic acid-labels for the ligation format has three elements. Two nucleic acid-labels and a linker oligonucleotide (FIG. 4). The nucleic acid-labels are designed such that 3' duplexes are not formed and extended by a nucleic acid polymerase. The first label has a chemically active group (such as, primary amine group) at its 5' end that allows it to be conjugated to one of two reporter conjugates, each of which must bind to a different binding site on the analyte. The first label also has to have a 3' hydroxyl group. The second nucleic acid-label has a chemically active group (such as, primary amine group) at its 3' end that allows it to be conjugated to the other of two reporter conjugates. The second label also has to have a 5' phosphoryl group. The third oligonucleotide is the linker oligonucleotide. Its sequence must have, respectively in tandem, a sequence that is complementary to the 3' (hydroxyl) end of the first oligonucleotide and a sequence that is complementary to the 5' (phosphoryl) end of the second nucleic acid-label. The ligation linkers may be designed with a replication inhibitor moiety at the 3' to avoid extension by the polymerase enzyme during the amplification part of the assay. Typical replication inhibitors moieties will include but are not limited to, dideoxynuleotides, 3-deoxynucleotide, a sequence of mismatched nucleosides or nucleotides, 3' phosphate groups and chemical agents. Within the context of the present invention cordycepin (3' deoxyadenosine) is preferred.

The replication inhibitor is covalently attached to the 3' hydroxy group of the 3' terminal nucleotide of the non-participatory detection probe during chemical synthesis, using standard cyanoethyl phosphoramidite chemistry. This process uses solid phase synthesis chemistry in which the 3' end is covalently attached to an insoluble support (controlled pore glass-CPG) while the newly synthesized chain grows on the 5' terminus. Within the context of the present invention, 3-deoxyribonucleotides are the preferred replication inhibitors. Cordycepin, 3-deoxyadenosine, is most preferred. Since the cordycepin will be attached to the 3' terminal end of the detection probe, the synthesis is initiated from a cordycepin covalently attached to CPG, 5-dimethoxytrityl-N-benzoyl-3-deoxyadenosine (cordycepin), 2-succinoyl-long chain alkylamino-CPG (Glen Research, Sterling, Va.). The dimethoxytrityl group is removed and the initiation of the chain synthesis starts at the deprotected 5' hydroxyl group of the solid phase cordycepin. After the synthesis is complete, the oligonucleotide probe is cleaved off the solid support leaving a free 2' hydroxyl group on the 3'-terminally attached cordycepin. Other reagents can also be attached to the 3' terminus during the synthesis of the non-participatory detection probe to serve as replication inhibitors. These include, but are not limited to, other 3-deoxyribonucleotides, biotin, dinitrophenol, fluorescein, and digoxigenin, which are also derivatized on CPG supports (Glen Research, Sterling, Va.; Clonetech Laboratories, Palo Alto, Calif.).

The minimum length of each nucleic acid-label should be long enough to allow for the 3' terminal end of the first nucleic acid-label to come in contact with phosphorylated 5' end of the second nucleic acid-label. The ligation linker must be able to simultaneously anneal to the ends of both labels, forming a stable duplexed structure that contains all three oligonucleotides. This structure brings together 3' hydroxyl group of the first label and the 5' phosphoryl group of the second label to close proximity so that a ligase enzyme can catalyze the formation of a phosphodiester bond between both groups. This results in the joining the two labels and the formation of a ligation-generated analyte-specific amplicon, as shown in FIG. 4.

One primer-binding site is associated with the second nucleic acid-label. Its sequence is at the 3' end of the label. The other primer-binding site will be on the 3' end of the complementary strand of the ASA and is formed after the first replication reaction in the amplification of the ASA.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Suitable methods of genetic engineering employed herein are described Sambrook, J., Fritsch, E. F. and Maniatis, T., *Molecular Cloning: A Laboratory Manual,* Second Edition, Cold Spring Harbor Laboratory Press, Cold Spring Harbor, N.Y. (1989) and in the instructions accompanying commercially available kits for genetic engineering.

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology,* Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Minn.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Oligonucleotide Synthesis

DNA oligonucleotide primers and reporter labels for both the overlap and ligation methods were prepared using standard β-cyanoethyl phosphoramidite coupling chemistry on controlled pore glass (CPG) supports, Beaucage et al., *Tetrahedron Lett.,* 22, 1859, 1981, in automated DNA oligonucleotide (Applied Biosystems Model 392, Foster City, Calif.). Three basic oligos were constructed and modified to produce overlap labels and ligation labels. These were T78 (SEQ ID NO:4), T 68 (SEQ ID NO:6) and T66 (SEQ ID NO:10). [See Table 1].

The 5' terminus of some of the oligonucleotide labels was derivatized using Aminolink 2™ (Applied Biosystems) or Uni-Link AminoModifierm ClonTech, Inc., Palo Alto, Calif.) to incorporate a primary aliphatic amine in the final coupling step of the synthesis. The same procedure is used for incorporating a phosphoryl group onto the 5' terminal nucleotide of T68 (SEQ ID NO:6). In this case, a 5' phosphate-ON™ phosphoramidite reagent (ClonTech, Inc.) is used. The 3' primary amine was also directly incorporated into the nucleic acid-label, T68 (SEQ ID NO:6), by automated synthesis using 3'-Amino-ON™ CPG, which incorporates the amine group onto the 3' hydroxyl terminal group. After the deprotection step, the DNA labels were ethanol precipitated. Additional purification steps to remove failure sequences from the preparation were not taken.

Figure 5:
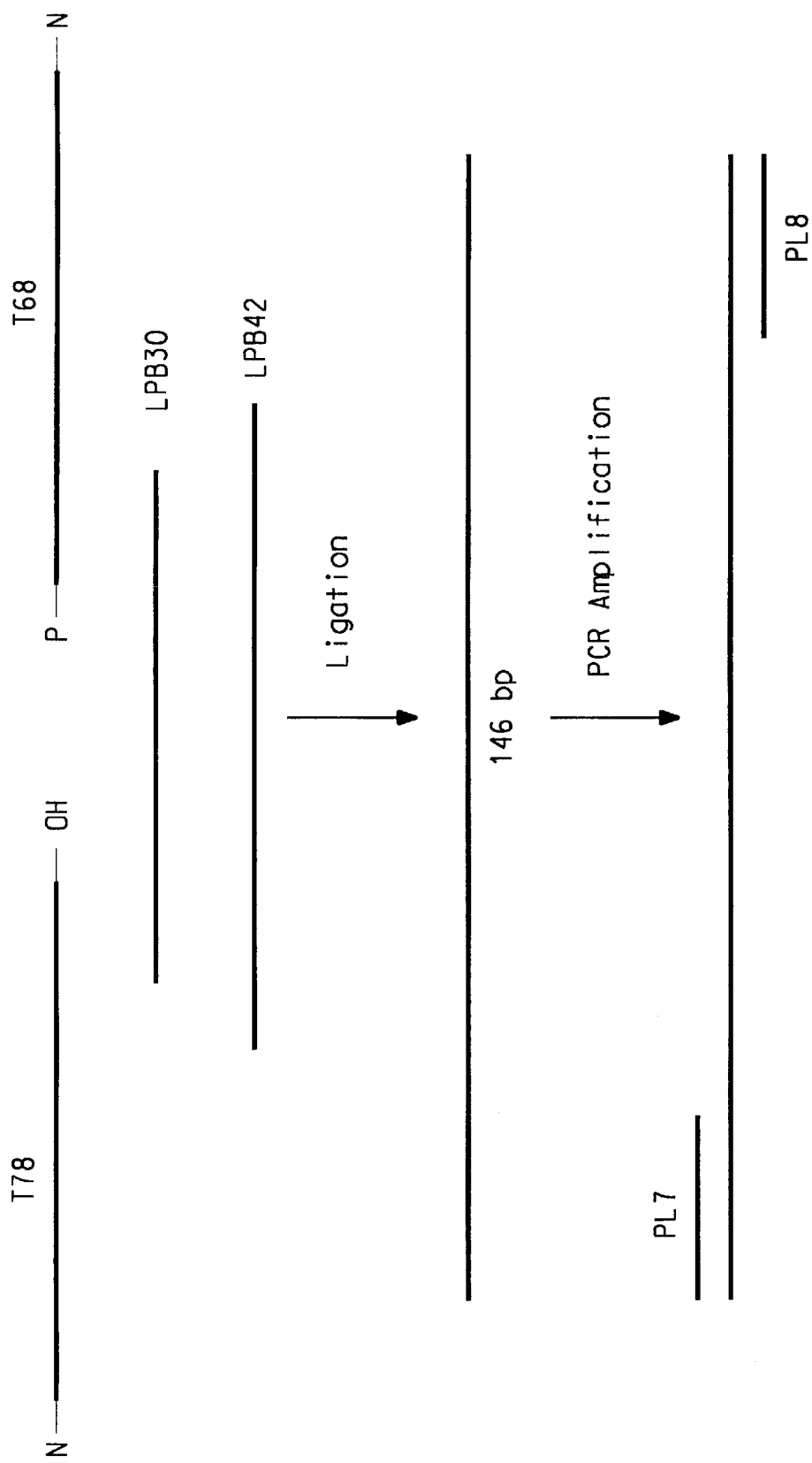
FIG. 5 is a diagram which illustrates the ligation-mediated DNA-label extension and PCR amplification.

DNA labels T68 (SEQ ID NO:6) and T78 (SEQ ID NO:4) were designed for the ligation format as shown in FIG. 5. The T78 (SEQ ID NO:4) label contains a 5' terminal amino group for covalent linkage to the antibody molecule and a 3' hydroxyl group that will participate in the ligation reaction. The T68 (SEQ ID NO:6) label was designed with a 5' phosphoryl group for the generation of the phosphodiester bond and a 3' amino group for covalent linkage to the antibody molecule. To promote the proximity of the 3' OH and 5' $PO_4$ groups necessary for phosphodiester bond formation by a T4 DNA ligase enzyme, two complementary oligonucleotides or ligase linkers were constructed. These ligation linkers were designed with a cordycepin group at the 3' to inhibit extension by the polymerase enzyme during the PCR part of the assay. Cordycepin was added to the 3' end of the ligation linker using a cordycepin coupled CPG column (Glen Research, Sterling, Va.), according to procedures supplied by the manufacturer. Upon hybridization to the 3' region of the T78 (SEQ ID NO:4) and the 5' region of the T68 (SEQ ID NO:6), the 3' hydroxyl and the 5' phosphoryl group from each the respective labels are held in adjacent nucleotide positions. The ligase enzyme can then catalyze the formation of a phosphodiester bond between the adjacent nucleic acid-labels, resulting in a 146 base joined, single-stranded oligonucleotide, which becomes the ASA. These joined-labels are subsequently amplified by PCR (FIG. 5).

Primers, overlap labels, ligation labels and ligation linkers used in the following examples are listed in Table 1 below.

TABLE 1

PCR Labels, PCR Primers and Ligation Linkers for Ligation and Overlap Approaches: Sequences of Primers, Labels, and Linkers

| | | Sequence (5'-3') |
|---|---|---|
| Primer | | |
| PL7 | | GCGAGGATGGCGAACAACAAGA (SEQ ID NO: 1) |
| INFP4 | | ACCGGGGGAGACGAAACTGCT (SEQ ID NO: 2) |
| PL8 | | TCGGGCGGAATGGGTGTGGT (SEQ ID NO: 3) |
| Label | | |
| T78 | | |
| | Ligation label | N-GCGAGGATGGCGAACAACAAGACTCTCTC TGCTTTCCCATCTATGCGTTAATTATGATCAAAC TCCAGGGGCCAGGGC-OH (SEQ ID NO: 4) |
| | Biotinylated Ligation label | B-GCGAGGATGGCGAACAACAAGACTCTCTC TGCTTTCCCATCTATGCGTTAATTATGATCAAAC TCCAGGGGCCAGGGC-OH (SEQ ID NO: 5) |

TABLE 1-continued

PCR Labels, PCR Primers and Ligation Linkers for Ligation and
Overlap Approaches: Sequences of Primers, Labels, and Linkers

| | | Sequence (5'-3') |
|---|---|---|
| T68 | | |
| | Ligation label | P-ACCGGGGGAGACGAAACTGCTAACTTATA TTCCTTCCTACTTTGCATCACCACACCCATTCC GCCCGA-NH$_2$ (SEQ ID NO: 6) |
| | Biotinylated Ligation label | P-ACCGGGGGAGACGAAACTGCTAACTTATA TTCCTTCCTACTTTGCATCACCACACCCATTCC GCCCGA-B (SEQ ID NO: 7) |
| | Overlap Label | N-ACCGGGGGAGACGAAACTGCTAACTTATA TTCCTTCCTACTTTGCATCACCACACCCATTCC GCCCGA-OH (SEQ ID NO: 8) |
| | Biotinylated Overlap Label | B-ACCGGGGGAGACGAAACTGCTAACTTATA TTCCTTCCTACTTTGCATCACCACACCCATTCC GCCCGA-OH (SEQ ID NO: 9) |
| T66 | | |
| | Overlap Label | N-GCGAGGATGGCGAACAACAAGACTCTCTC TGCTTTCCAATCTATGCGTTAATTATGATCTCGG GCG-OH (SEQ ID NO: 10) |
| | Biotinylated Overlap Label | B-GCGAGGATGGCGAACAACAAGACTCTCTC TGCTTTCCAATCTATGCGTTAATTATGATCTCGG GCG-OH (SEQ ID NO: 11) |
| Ligation Linker | | |
| dA PB42* | | AGCAGTTTCGTCTCCCCCGGTGCCCTCGCC CCTGGAGTTTG-dA (SEQ ID NO: 12) |
| dA PB30* | | TTCGTCTCCCCCGGTGCCCTCGCCCCTGG-dA (SEQ ID NO: 13) |

OH = hydroxyl group, B = biotin, dA = cordycepin (3'dA), P = phosphoryl group, N = primary amino group Preparation of Oligonucleotide-antibody Conjugates Synthesis of the two DNA-labeled antibody conjugates was accomplished in four phases. In this approach, 5' amino-modified oligonucleotides and analyte-specific antibodies were independently activated by means of separate heterobifunctional cross-linking agents. The activated oligonucleotides and antibodies were then mixed to facilitate spontaneous coupling of the DNA-label with the antibody. Specific conditions and protocols for each phase of the synthesis are described below:

(1) Acetylthioacetyl Derivatized DNA

Amino-modified reporter oligonucleotides were reacted with N-succinimidyl S-acetylthioacetate (SATA) as follows. An aliquot of the amino-modified oligonucleotide preparation, 50–60 nmoles, was added to 667 μL reaction mixture containing 100 mM sodium bicarbonate buffer (pH 9.0), 13.3 mg/mL SATA, and 50% dimethyl formamide (DMF). After 30 min at 25° C., the reaction mixture was immediately applied to a 1×20 cm Sephadex® G-25 column (Pharmacia Biotech, Inc., Piscataway, N.J.) and eluted at room temperature with 100 mM sodium phosphate buffer, pH 6.5, at a flow rate of ~1 mL/min. The absorbance of the effluent was monitored at 280 nm using a Pharmacia Model 2138 UVICORD S Monitor, and fractions were collected on a Pharmacia Model Frac-100 fraction collector (Pharmacia Biotech, Inc., Piscataway, N.J.). Two-milliliter fractions were collected, and those containing the acetylthioacetyl-modified oligonucleotides were pooled. These fractions were concentrated to a final volume of approximately 1.0 mL using Amicon Centricon™ 3 concentrators (Amicon, Inc., Beverly, Mass.) and a Sorvall® SM-24 rotor in a RC-5B centrifuge (Sorvall®, E. I. du Pont de Nemours and Company, Wilmington, Del.), spun at 7500 rpm (7000 × g) for 45 min at 20° C. The resulting samples were pooled, and further concentrated using the same procedure in a second set of Centricon™ 3 concentrators. The acetylthioacetyl-modified oligonucleotide concentrate (approximately 1.0 mL) was recovered using the protocol recommended by the manufacturer (Amicon, Inc., Beverly, Mass.) and was saved at 20° C. in the dark until it was needed for the final attachment of DNA label to reporter antibody.

(2) Maleimide-modified Antibodies

The reporter antibodies were derivatized with maleimide groups using sulfosuccinimidyl 4-[N-maleimidomethyl] cyclohexane-1-carboxylate (sulfo-SMCC). An aliquot containing 25 mnoles of antibody was added to a reaction mixture (2.2 mL) containing 100 mM sodium phosphate buffer (pH 7.0), 1.2 mg/mL sulfo-SMCC, 1.5% DMF. (Note: The antibody modification reaction is started 75 min after beginning the preparation of the acetylthioacetyl-derivatized oligonucleotide. This timing is essential to minimize the deactivation of maleimide groups present in an aqueous solution, prior to the final conjugation reaction.) After the mixture had reacted for 30 min at 25° C., it was immediately applied to a 1×20 cm Sephadex® G-25 column and eluted at room temperature with 100 mM sodium phosphate buffer, pH 6.5 at a flow rate of ~1 mL/min. The effluent was monitored and column fractions were collected as previously described for a Sephadex® G-25 column. The first peak fractions (2.0 mL/fraction), which contained the maleimide-modified antibody, were pooled (4–6 mL) into one tube. The reaction product was ready for coupling to the modified oligonucleotides.

(3) DNA Oligonucleotide-antibody Conjugations

The pooled maleimide-modified antibody fraction was immediately added to a 15 mL Falcon® 2059 tube (Becton Dickinson, Cockeysville, Md.). The concentrated acetylthioacetyl-modified oligonucleotides (approximately 1.0 mL) were added to the same tube and mixed well. The coupling reaction was initiated by adding 75 μL of 1 M hydroxylamine hydrochloride (Pierce Chemical Co., Rockford, Ill.), pH 7.0, 50 mM EDTA and mixing well. The reaction mixture was transferred to an Amicon Model 3 mini-ultrafiltration stirred cell fitted with a YM10 membrane filter (Amicon, Inc., Beverly, Mass.). The cell was connected to a helium source adjusted to 60 psi. The coupling reaction proceeded with stirring at room temperature while the entire vessel was covered with aluminum foil to reduce exposure to light. The reaction mixture was concentrated to approximately 1.0 mL, removed from the MiniCell apparatus, and transferred to a 4.0 mL amber vial (Wheaton, Inc., Millville, N.J.). This vial was incubated in the dark at room temperature on a Lab Quake™ tube rotator (Labindustries, Inc., Berkeley, Calif.) until the total reaction time reached 2 h. The reaction was terminated by the addition of 10 μL of 10 mM N-ethylmaleimide in DMF.

(4) Purification of the Oligonucleotide-antibody Conjugates

The initial step in the purification of the conjugates remove much of the unreacted, free oligonucleotides and failure sequences using Centricon™ 100 microconcentrators (Amicon, Inc., Beverly, Mass.). The conjugate preps were then further purified by gel filtration high pressure liquid chromatography (HPLC). The HPLC system consisted of a Waters Model 600E multisolvent delivery system and Model-996 photodiode array detector (Milford, Mass.). Separation was accomplished using a mobile phase sodium phosphate buffer (200 mM, pH 7.0) at a flow rate of 1 mL/min through a 9.4×250 mm Zorbax® GF-250 column (MAC-MOD Analytical, Inc., Chadds Ford, Pa.). Injections of the conjugate (200 μL) were made with a Waters 700 Satellite WISP automated injection system. The first HPLC peak fractions (0.3 mL/fraction) were mixtures of the oligonucleotide-antibody conjugate and the maleimide-modified antibody reaction component that were virtually free of the acetylthioacetyl-modified oligonucleotide precursor peak.

Fractions containing the conjugate were determined by testing the HPLC fractions with a immuno-probe assay. The assay uses a biotinylated probe, which has a sequence that is complementary to the sequence of the reporter conjugate's DNA label. The reporter conjugate is first captured by anti-immunoglobulin (anti-IgG). Then, the biotinylated probe added and is allowed to hybridize to DNA label. Next, a streptavidin labeled with alkaline phosphotase is added to bind to the biotin labels of the probe. Colored alkaline phosphotase substrates are added as assay reporter. The fractions, where the DNA-labeled reporter conjugate is located, are determine by reading the results of the alkaline phosphotase reaction on microplate spectrophotometric reader. The fractions containing the conjugate were pooled and concentrated by microconcentrator centrifugation and stored at 4° C.

Antibodies

Antibodies used in the test examples were obtained from the Untied States Army Medical Research Institute for Infectious Disease (1425 Porter Street, Fort Detrick, Md. 21702). The equine polyclonal Clostridium botulinum A antibodies were prepared by immunizing houses with adjuvant containing attenuated botulinum toxin A. Horse antiserum was harvested and the antibodies affinity purified using an affinity column prepared by immobilizing a recombinant C-fragment of botulinum type A toxin cat. number CFOO1A (Ophidian Pharmaceuticals Inc., Madison, Wis. 53711) on cyanogen bromide activated Sepherose 4B cat. number 17-0430-01 (Amersham Pharmacia Biotech, Inc. 800 Centennial Ave., Piscataway, N.Y. 08855-1327). Following affinity purification the purified antibody was then concentrated by molecular filtration and used for preparation of DNA antibody conjugates. The mouse monoclonal IgG antibodies specific to the botulinum type A toxin C-fragment were prepare using standard hybridoma tissue culture techniques (Ed. Harlow and D. Lane, in *Antibodies a Laboratory Manual,* Cold Spring Habor Laboratory (1988) pages 139 to 280). The monoclonal antibody was purified from ascites fluid over protein A bead column (Ed. Harlow and D. Lane, in *Antibodies a Laboratory Manual,* Cold Spring Habor Laboratory (1988) pages 283 to 342).

Example 1

Detection of *Clostridium Botulinum* Toxin A Fragment

Example 1 illustrates the overlap method of forming the ASA in a heterogeneous format for the detection of C-fragment of botulinum toxin A.

a) Preparation of Immobilized Capture Reagent (Antibody)

The capture monoclonal antibody was covalently linked to carboxylated ⅛ (polystyrene beads (Polysciences, Inc., Warrington, Pa.) by the carbodiimide method, described as follows.

Fifty beads were suspended in 1.3 mL of 0.02 M sodium phosphate buffer (PB), pH 4.5. To this was added 1 mL of a 2% 1-(3-dimethylamino-propyl)-3-ethyl carbodiimide hydrochloride in 0.02 M PB buffer, pH 4.5, dropwise. The bead suspension was mixed for 3 hours at room temperature using end-to-end mix. Next, the supernatant was drained and the beads washed in 0.02 M PB, pH 4.5 and drained. This process was repeated three times to remove unreacted carbodiimide. The beads were then resuspended in 1.3 mL of 0.2 M borate buffer, pH 8.5. The antibody to be coupled was diluted to the appropriate concentration (6 μg/mL) in 0.2 M borate buffer, pH 8.5, and added to the beads. The mixture was allowed to mix overnight at room temperature end-over-end. Fifty μliters of 0.25 M ethanolamine was added to the mixture, which was then mixed for 30 minutes. The beads were resuspended in 2% BSA solution and allowed to mix for 1 hour to block any remaining non-specific protein binding sites. The beads were stored in PBS, pH 7.4, containing 10 mg/mL BSA, 5% glycerol and 0.1% sodium azide.

For passive adsorption, the solid-phase was coated with 50 μL of antibody per microtiter plate well or bead (6 μg/mL in 100 mM sodium bicarbonate, pH 9.5). The microtiter plate wells (or solid-phase) was washed several times with the TBST wash buffer (25 mM Tris, pH 7.4, 150 mM NaCl, 0.05% Tween-20) to remove the unbound antibody. The wells (or solid-phase) was then blocked with the block solution containing 2% BSA, 10 mM sodium phosphate, pH 7.4, 150 mM NaCl, 10% β-lactose, 0.02% $NaN_3$. After one hour of incubation, the blocking solution was removed and the wells washed as previously described.

b) The Reporter Conjugates

For the overlap format (Examples 1, 2, 3 and 5), the DNA labels, T66 and T68 (Table 1), were covalently attached to their respective antibodies through 5' terminal amine groups. They were designed such that the 7 bases of the 3' ends of each oligonucleotide were complementary to each other and thus, served as extension primers to produce the double-stranded ASA. The amplification primers, PL7 (SEQ ID NO:2) and INFP4 (SEQ ID NO:1), were designed such that they were complementary to the ASA (127 bp) rather than the individual labels. Thus, the formation and amplification of the 127 bp full length ASA will occur only when the labels are in close proximity to one another, as would happen when antibodies are specifically bound to their adjacent epitopes.

The temperatured of the reactions were strickly controled. A 7 to 10 bp overlap of the 3' ends of the labels, which has an approximate $T_m$ of 25° C., was used to avoid formation of the duplex at 37° C. (the incubation temperature used for antibody-analyte binding). If the duplex was stable at temperatures exceeding 37° C., it could form when one antibody is bound nonspecifically to the plate and the other in solution. The annealed labels would then be extended, the 127 bp product formed and amplified, and the resulting false-positive product would be detected by gel electrophoresis. However, after the analyte-reporter complex is formed and the temperature reduced to 25° C., the 3' overlap is allowed to form. Only those antibodies bound in close proximity to one another (specific binding) will anneal the overlapped 3' termini of their labels.

The overlapped duplex was extended using a DNA polymerase Taq I DNA polymerase. The annealing and extension period was 3 minutes. Where the assay used a PCR microtiter plate then the newly formed ASA was then subjected to amplification directly. Where the solid-phase was a bead, it was transferred to a PCR plate and then subjected to amplification.

c) Assay Conditions And Protocol

Immunoassay

Fifty microliters aliquots of different concentrations of recombinant C fragment of botulinum A (OPHIDIAN Pharmaceuticals, Madison, Wis.) were incubated overnight at room temperature with the antibody-linked polystyrene beads in a microtiter plate (Falcon®3911, Becton Dickinson, Oxnard, Calif. 93030). The analyte concentrations used were 3-fg, 30-fg, 300-fg, 3-pg, 30-pg, 300-pg and 3-ng. TBST buffer was used for negative control. The beads were washed several times with 350 µL of the TBST wash buffer. To each bead in the microtiter plate well, 100 µL of a equimolar mixture of appropriately diluted two different antibody-DNA conjugates were added and allowed to incubate at 37° C. for 15 minutes. The beads were then washed several times with the TBST wash buffer.

ASA Amplicon Formation Amplification by PCR

Where beads were used as the solid-phase medium the beads were transferred to PCR-microtiter plate wells prior to DNA amplification. Before the transfer of the beads to the plate, the microtiter plate was first trimmed for insertion in to the 96-well sample block of a Perkin-Elmer Gene-Amp™9600 thermal cycler (Norwalk, Conn.). Next, the wells were filled with the 30 µL of sterile double-distilled water. Then, the beads are transferred to the wells. Five microliters of primers, INFP4 (SEQ ID NO:2)and PL7 (SEQ ID NO: 1), (250 pmol/primer) were added. This was followed by the addition of 15 µL of PCR reaction mixture (10 mM Tris-HCl (pH 8.3), 50 mM KCl, 1.5-mM $MgCl_2$, 0.2 mM/ea dNTP's, and 1.25 units Amplitaq DNA polymerase) to a final reaction volume of 50 µL. The reaction mixture was covered with 20 µL of liquid wax (Chill-Out™, MJ Research Inc., Watertown, Mass.).

The microtiter plate was covered and sealed with plate sealing tape (Costar, Inc., Cambridge, Mass.). The microtiter plate was inserted in to a 9600 thermal cycler (Perkin-Elmer Corp.). A tray assembly was placed over top of the sealed microtiter plate. The cover of the thermal cycler was tightened in place to exert even pressure over the plate. The DNA label sequences were annealed and the ASA formed by polymerase extension at 25° C. for 3 min. The labels extensions were completed at 72° C. for 2 min. The full-length ASA product was then amplified (PCR) using 30 cycles as follows:

denaturation at 94° C. for 10 sec, annealing at 60° C. for 15 sec, and extension at 72° C. for 10 sec After completing the amplification cycles, the final chain extension was at 72° C. for 45 sec. Samples were then ramped to at 4° C. and maintained at that temperature until sample analysis.

Detection and Analysis of PCR Products

Amplified ASA from each assay well were separated on 4% NuSieve® 3:1 agarose (FMC BioProducts, Rockland, Me.) in 0.5 × TBE buffer (Digene Diagnostics, Inc., Silver Spring, Md.) containing 0.3 µg/mL of ethidium bromide. An aliquot of 15 µL from the amplified samples was mixed with 3 µL of gel loading buffer (30% glycerol and 0.25% bromophenol blue) and loaded onto the agarose gel (8.5~6.0× 0.5 cm: 25 mL agarose sol). Gel electrophoresis was carried out by applying 150V (or 5.9 V/cm) to the gel for 25 min.

The ethidium bromide-stained DNA bands were visualized and digitally recorded using an Eagle Eye II Still Video System (Stratagene, La Jolla, Calif.). The digitized image was further analyzed by using NIH Image V1.61 software to measure the intensity (pixel intensities per unit area) of the PCR product bands.

Figure 6:
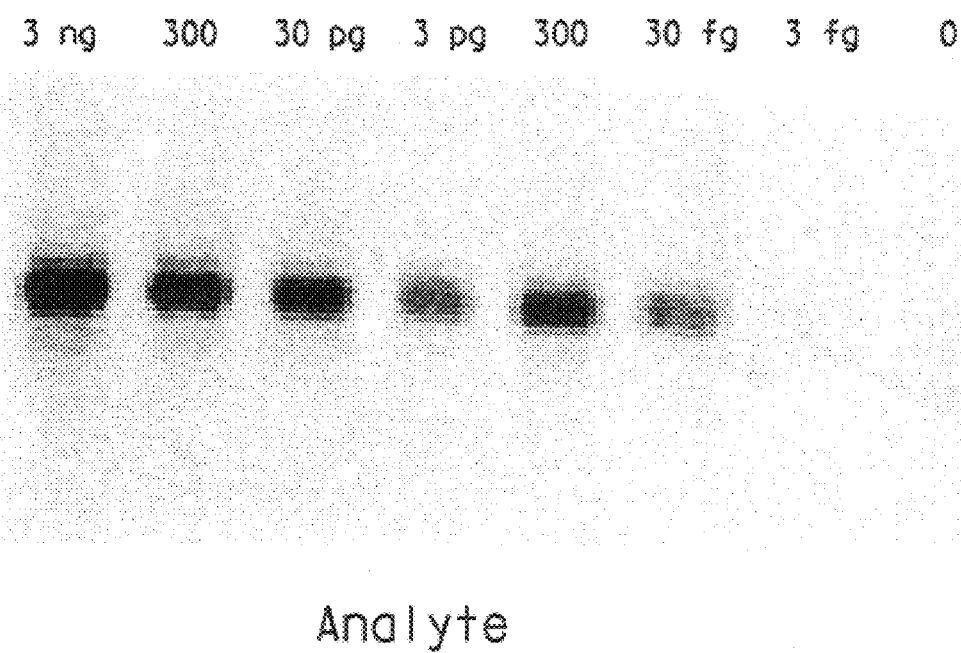
FIG. 6 is an image of a gel produced by agarose gel electrophoresis showing amplified ASA product produced by the overlap approach over decreasing concentrations of analyte.

FIG. 6 shows the analysis of PCR ASA products by agarose gel electrophoresis. With the antibody system used, the least amount of analyte that could be differentiated from blank was 30 fg.

Example 2

ASA Formation by Overlap Using Streptavidin-Captured Biotinylated DNA Labels

Example 2 illustrates the use of the present method, employing a biotin -streptavidin avidin binding-pair. Biotinylated DNA labels, T66-B (SEQ ID NO:11) and T68-B (SEQ ID NO:9) (Table 1), were designed such that the 7 bases of the 3' ends of each oligonucleotide were complementary to each other. Each DNA label was biotinylated at the 5' end using phosphoramidite reporter labels (label-ON reagents, ClonTech Laboratories, Inc., Palo Alto, Calif.), as described above.

Figure 7:
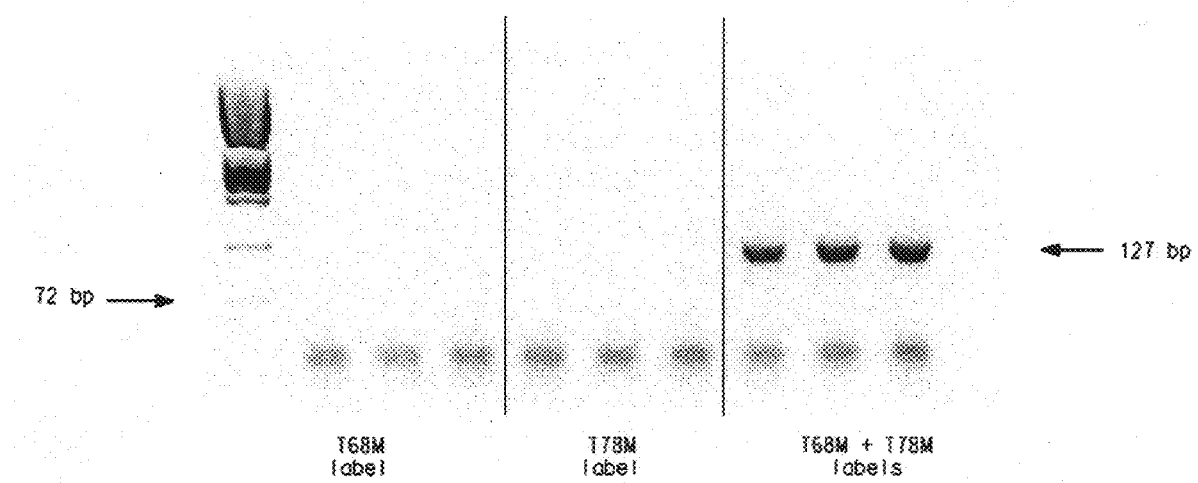
FIG. 7 is an image of a gel produced by agarose gel electrophoresis showing amplified ASA product of 127 bases produced by the overlap approach, where the product is produced only in the presence of both labels.

A 96-well, PCR microtiter plate (Concord 25, MJ Research, Watertown, Mass.) was coated with of 6 ug/mL streptavidin (50 µL/well) for 1 hour at room temperature. The plate was washed in TBST (25 mM Tris, pH 7.4, 150 mM NaCl, 0.05% Tween-20) with an automatic plate washer. The wells were then treated with 200 µL of blocking buffer (10 mM sodium phosphate, pH 7.4, 150 mM NaCl, 2% BSA, 10% µ-lactose, 0.02% sodium azide) for 1 hour and washed again, three times. Approximately $10^{12}$ copies of biotinylated T68-B (SEQ ID NO:9), T66-B (SEQ ID NO:11), or both labels were added to microtiter plate wells. Then, the samples were incubated at room temperature for 1 hour. Sample wells were then washed several times with TBST wash buffer as previously described. Each well received an aliquot of reaction mix containing 50 pmol each of primers, PL7 (SEQ ID NO: 1) and INFP4 (SEQ ID NO:2), 200 µM dNTPs, 1.5 units of Taq polymerase (Perkin-Elmer Corp., Norwalk, Conn.) in a final volume of 50 µL PCR buffer (50 mM KCl, 10 mM Tris-Cl, pH 8.4, 1.5 mM $MgCl_2$, 0.01% gelatin). The microtiter plate was covered and sealed with plate sealing tape (Costar, Inc., Cambridge, Mass.). The microtiter plate was then placed in a 9600 thermal cycler (Perkin-Elmer Corp.). A tray assembly was placed over top of the sealed microtiter plate. The cover of the thermal cycler was tightened in place to exert even pressure over the plate. To allow for the formation of the ASA, the 7 bases at the 3' ends of the two DNA labels are annealed to each other and extended. An annealing and primary extension steps were performed at 25° C. for 3 min. These were then followed by a polishing extension step at 72° C. for 2 min. The full-length product was then amplified for 35 cycles as follows:

denaturation at 94° C. for 10 sec, annealing at 60° C. for 15 sec, and extension at 72° C. for 10 sec After completing the amplification cycles, the is a final chain extension at 72° C. for 45 sec. The samples were then cooled to 4° C. Aliquots of the PCR products (8 µL) were mixed with 10× gel loading buffer (30% glycerol and 0.25% bromophenol blue) and separated on 2% agarose gels in 0.5× TBE buffer (Digene Diagnostics, Inc., Silver Spring, Md.) containing 0.5 ug/mL ethidium bromide. The ethidium bromide-stained DNA bands were visualized with a UV transilluminator as described earlier. FIG. 7 shows that the full-length amplified ASA product (127 bp) is present only when both labels are bound to the well.

Example 3

Effect of Low Label-label Proximity Mimicking the Effects of Nonspecific Binding by Decreasing the Label-label Proximity Example 3 demonstrates the relationship between assay sensitivity and label-label proximity. The assay employed the overlap method for ASA formation in a heterogeneous format and all materials protocols were followed essentially as described in Example 2 except for the variations in DNA label and streptavidin concentrations. The experiment illustrated that as the distance between the immobilized DNA labels increased, there was a corresponding decrease in assay sensitivity.

Figure 8:
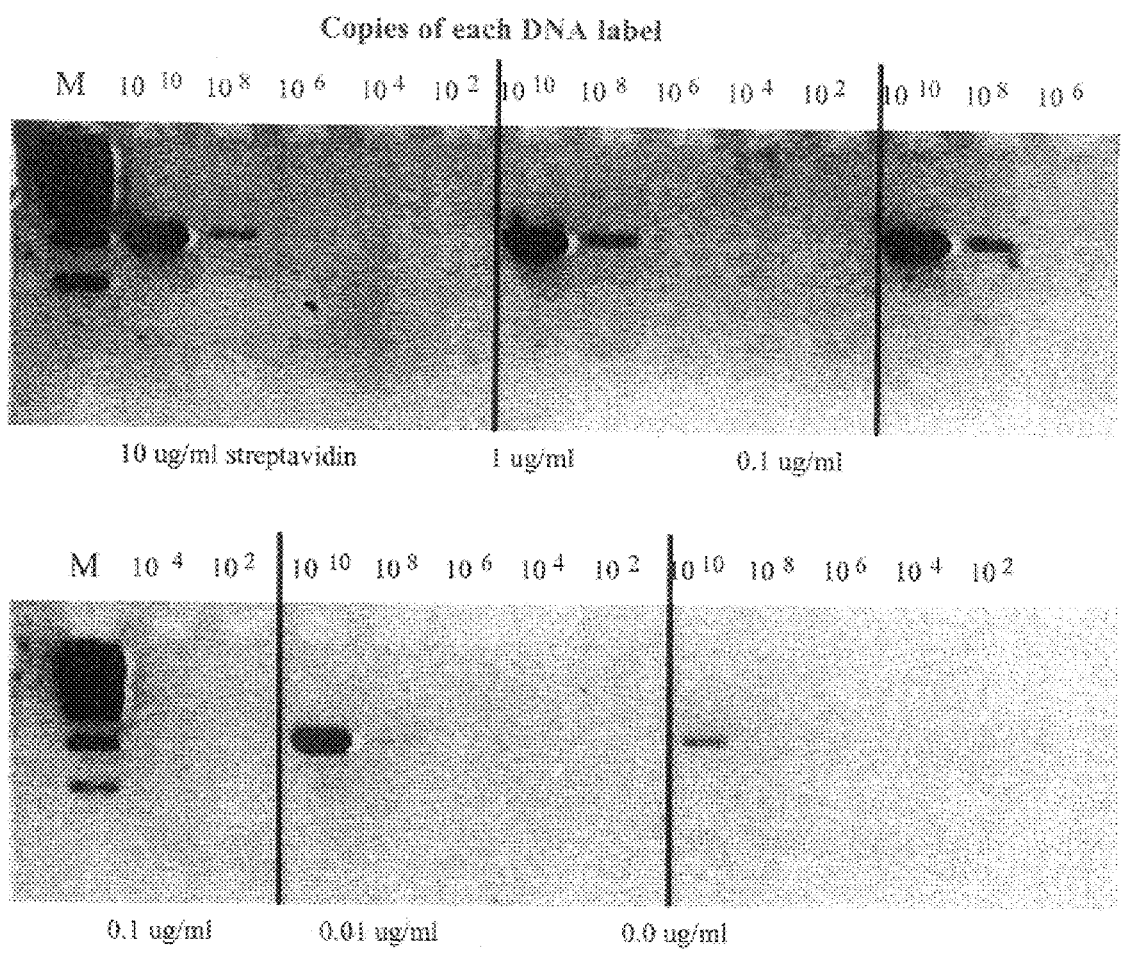
FIG. 8 is an image of a 2% agarose electrophoresis gel showing the production of ASA amplification products over decreasing concentrations of streptavidin capture reagent and DNA label.

Microtiter plates were coated with decreasing concentrations of streptavidin (10, 1, 0.1, 0.01, or 0 ug/mL). The plates were blocked and washed as described above (Example 2). The biotinylated DNA labels were added together at decreasing concentrations ($10^{10}$, $10^8$, $10^6$, $10^4$, $10^2$ copies) across the five streptavidin concentrations and samples were incubated for 1 hr at room temperature. The wells were then washed with TBS/Tween. PCR amplification was performed as above and 8 µL of the samples were run on a 2% agarose gel. FIG. 8 shows that as the streptavidin concentration decreases, and the labels become spatially separated, the formation of the 127 bp ASA amplified product also decreases.

As shown in FIG. 8, where the concentration of streptavidin is zero, only the high concentration of $10^{10}$ copies of each sample was able to produce an amplification product. Even here, it is likely that the formation of product for this sample was probably the result of the high concentration of labels interacting with each other in solution.

Example 4

ASA Formation by DNA Ligation Using Streptavidin Captured Biotinylated DNA Labels Example 4 illustrates a detection of a C-Fragment of botulinum Toxin A analyte in a heterogeneous format where the ASA was created by the ligation method, employing two DNA labels and a ligation linker, the linker terminated with cordycepin as described above.

DNA labels T68 and T78 (Table 1) were designed and labled according to the procedures described in the GENERAL METHODS. The relevant DNA lables are all shown in Table 1, above and in FIG. 5.

To promote the proximity of the 3' OH and 5' $PO_4$ groups necessary for phosphodiester bond formation by a T4 DNA ligase enzyme, two complementary oligonucleotide ligation linkers were designed [LPB30 (SEQ ID NO:13) and LPB42 (SEQ ID NO: 12), Table 1] Upon hybridization of the ligation linker to the 3' region of the T78 and the 5' region of the T68, the double-stranded region provide the necessary substrate for ligation of the two nucleic acid-labels by the T4 DNA ligase to form the ASA. The resulting ligation produces a 146 bp analyte-specific amplicon, which is subsequently amplified by PCR, as illustrated in FIG. 5.

To enable the ligation reaction, the 5' and 3' terminal amino groups in the T78 and T68 labels, respectively, were substituted with a biotin group. These provided a non-covalent attachment onto a solid support that mimicked the binding of the reporter antibodies, bringing both labels within close proximity of each other.

96-well PCR microtiter plates (Concord 25, MJ Research, Inc., Watertown, Mass.) were coated with 50 $\mu$L/well of a streptavidin (6 ug/mL) in a 100 mM sodium bicarbonate, (pH 9.5). Passive coating was allowed to proceed at 4° C. overnight (16–18 h). After coating, the plates were washed in assay diluent/wash buffer, (TBST: 25 mM Tris, pH 7.4, 50 mM sodium chloride, 0.05% Tween-20), and the non-adsorbed sites in the microtiter wells were blocked with 200 $\mu$L/well of blocking solution (PBS-BLA buffer: 10 mM sodium phosphate, pH 7.4, 150 mM sodium chloride, 2% BSA, 10% b-lactose, 0.02% sodium azide). Both the blocking and washing steps were performed as previously described (Example 2).

Biotinylated T68 (SEQ ID NO:7)and T78 (SEQ ID NO:5) labels were added in equimolar amounts (1, 0.5, 0.1, 0.001, and 0.0001 nanomoles/reaction) in a total volume of 50 $\mu$L/well of the TBST buffer or water. Incubation at room temperature proceeded for 1 h after which the reaction wells were washed as previously described. Next, 50 $\mu$L of a ligation mix containing 1× Ligase buffer (30 mM Tris-HCl, pH 7.8, 10 mM $MgCl_2$, 10 mM Dithiothreitol (DTT), 0.5 mM ATP, T4 DNA ligase enzyme (1 Weiss unit), and ligation linker [LPB30 (SEQ ID NO:13) or LPB42 (SEQ ID NO:12) at 1 nmol per reaction] were added. The reaction was incubated for 30 min at 30° C. and the wells were washed as previously described.

The amplification reaction of the ligated ASA was done in a final volume of 50 $\mu$L containing 10 mM Tris-HCl (pH 8.3), 50 mM KCl, 1.5 mM $MgCl_2$, 200 $\mu$tM dATP, 200 $\mu$M dCTP, 200 $\mu$M dGTP, 200 $\mu$M dTTP, 100 nM each of the amplifying primers, and 1.25 units Taq DNA polymerase (AmpliTaq®, Perkin-Elmer Corp., Norwalk, Conn.).

The PCR reaction was performed as follows. Thirty microliters of sterile distilled water was added to each sample well of the microtiter plate. A 5 $\mu$L aliquot of the primer mix was added to the sample wells, followed by a 20 $\mu$L aliquot of liquid wax (Chill-Out™, MJ Research Inc., Watertown, Mass.). The microtiter plate was inserted in to a 9600 thermal cycler (Perkin-Elmer Corp.). A tray assembly was placed over top of the sealed microtiter plate. The cover of the thermal cycler was tightened in place to exert even pressure over the plate. The thermal cycler was ramped to 95° C. for five min (initial denaturation step) and then held at 72° C. for a hot start (15). A master mix containing the reaction buffer, sterile water, $MgCl_2$, and dNTPs was heated to 72° C. and then the Taq DNA polymerase was added. A 15 µL aliquot of master mix at 72° C. was added to each test well, dispensing below the liquid wax layer. The microtiter plate was covered and sealed with plate sealing tape (Costar, Inc., Cambridge, Mass.). A tray assembly was placed over the sealed microtiter plate to exert even pressure and even temperature exchange during thermal cycling. Amplification was performed in 30 cycles using the following thermal cycling conditions:

denaturation at 94° C. for 10 sec, annealing at 60° C. for 15 sec, and extension at 72° C. for 10 sec After completing the amplification cycles, the is a final chain extension at 72° C. for 45 sec. The cycler was then ramped to 4° C. and held until sample analysis.

Amplified ASA products from each assay well were separated on 4% NuSieve® 3:1 agarose (FMC BioProducts, Rockland, Me.) in 0.5 × TBE buffer (Digene Diagnostics, Inc., Silver Spring, Md.). An aliquot of 15 µL from the amplified ASA samples was mixed with 3 µL of gel loading buffer (30% glycerol and 0.25% bromophenol blue) and loaded onto the agarose gel (8.5×6.0×~0.5 cm: 25 mL agarose sol). Gel electrophoresis was carried out by applying 150 V (or 5.9 V/cm) to the gel for 25 min. After electrophoresis the agarose gels were stained using ethidium bromide (0.3 µg/mL). The ethidium bromide-stained DNA ASA bands were visualized and recorded using an EagleEye II System.

Figure 9:
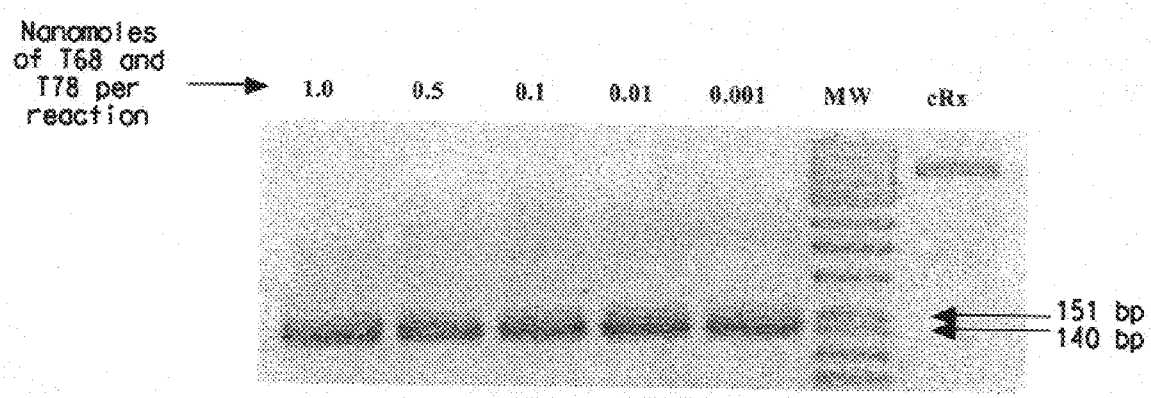
FIG. 9 is an image of a agarose electrophoresis gel showing the production of a 146 bp amplification product, produced by amplification of the ASA, formed by the ligation approach.

FIG. 9 shows the results from the PCR amplification of the ligated ASA. As seen in FIG. 9, an amplified ASA product of the expected molecular size (146 bp) was obtained. This results illustrates the feasibility of the present method of analyte detection where the ASA is formed via ligation as opposed to DNA overlap.

The T68 (SEQ ID NO:7) and T78 (SEQ ID NO:5) labels were added to a streptavidin coated solid support in concentrations ranging from $10^{-2}$ to $10^{-12}$ nmoles per reaction. Amplification of the ligated ASA is visible up to a concentration of $10^{-5}$ nmoles per reaction ($10^9$ labels) in the presence of either ligation linker (LPB30 or LPB42). A definitive demarcation in the presence of amplified product is visible at the mentioned concentration ($10^{-5}$ nmoles), suggestive of a definitive requirement in the effective concentration and therefore proximity of the DNA labels.

Example 5

ASA Formation by Nucleic Acid Table Overlap in Homogeneous Assay Format

Example 5 illustrates the feasibility of the instant method in a homogeneous format where the analyte is not immobilized prior to the formation of the analyte dependent reporter complex.

The homogeneous assay is performed by incubating the analyte (C-Fragment of botulinum Toxin A, described in Example 1) and the conjugates in order to permit the antigen-antibody interaction to proceed. Specifically, serial dilutions of the analyte (C-Fragment of botulinum Toxin A) are prepared in 1× PCR buffer (no Magnesium) to provide a total from 3 micrograms to 3 picograms per 10 microliter aliquot. The Ab-DNA reporter conjugates are also diluted in the 1× PCR buffer (no Magnesium) to an appropriate concentration. The reported working dilution could be in the $10^{-4}$, $10^{-5}$, or $10^{-6}$ dilution for each separate conjugate. Once diluted, equal volumes of the conjugates are mixed in order to prepare the working conjugate mix for the assay. In order to establish a convenient volume to aliquot the conjugate mix, an additional 1:5 dilution in 1× PCR buffer may be introduced thus providing a volume of 5 µL of aliquoted conjugate working dilution into the assay manipulations. The third reagent added to the reaction is an aliquot of 15 µL of water to complete the 25 µL total reaction volume that undergoes incubation for the antigen-antibody reaction to take place. Temperatures for incubation could range within the permissible temperature tolerance of the antigen-antibody interaction, for example between 25° C. and 45° C.

After a 30 minute incubation the reaction is supplemented with 5 µl of the working primer dilution (containing both primers for the PCR amplification), and 15 µL of the PCR Master Mix for amplification. The reaction is incubated as described before for the NBI-PCR protocol. The ASA amplification products will be separated and visualized by gel electrophoresis where detection of at least 30 fg of product will be measurable.

What is claimed is:

1. A method for the detection of a non-nucleic acid analyte comprising:
   (i) contacting at least one non-nucleic acid analyte having at least two reporter conjugate binding sites with at least two reporter conjugates, said reporter conjugates each comprising:
   a) one member of a binding pair having specificity for at least one reporter conjugate binding site on said analyte;

b) a nucleic acid label;
wherein said analyte binds to said reporter conjugate forming an analyte dependent reporter complex;
(ii) contacting said analyte dependent reporter complex with a enzyme composition wherein the nucleic acid labels on said reporter conjugates are joined to form an analyte specific amplicon;
(iii) contacting the analyte dependent amplicon with an replication composition wherein amplification products are produced; and
(iv) detecting said amplification products.

2. A method according to claim 1 wherein said non-nucleic acid analyte at step (i) is optionally immobilized on a solid support.

3. A method according to claim 1 wherein said enzyme composition comprises a DNA polymerase and wherein said nucleic acid labels on said reporter conjugates are joined by an overlap at each 3' end.

4. A method according to claim 1 wherein said enzyme composition comprises a DNA ligase and wherein said nucleic acid labels on said reporter conjugates are enzymatically joined by means of a ligation linker comprising a replication inhibitory moiety.

5. A method according to claim 3 wherein said overlap comprises from about 10 bases to about 30 bases.

6. A method according to claim 2 wherein said solid support is comprised of materials selected from the group consisting of polyethylene, polypropylene, poly(4-methylbutene), polystyrene, polymethacrylate, poly(ethylene terephthalate), nylon, poly(vinyl butyrate), glass, ceramics, metal and metal oxides.

7. A method according to claim 1 wherein said one member of a binding pair is selected from the group consisting of an antigen, antibody, hapten, nucleic acid, a nucleic acid aptamer, biotin, streptavidin, avidin, folic acid, folate binding protein, protein A protein G, immunoglobulins, epoxide, malaimide and sulfhydryl reactive groups.

8. A method according to claim 1 wherein the at least two reporter conjugates have different specificities for different reporter conjugate binding sites on said analyte.

9. A method according to claim 1 wherein said nucleic acid labels are of different lengths.

10. A method according to claim 1 wherein said nucleic acid labels are of different nucleotide sequence.

11. A method according to claim 1 wherein said nucleic acid labels are from about 30 bases to about 1000 bases in length.

12. A method for the detection of a non-nucleic acid analyte comprising:
(i) immobilizing at least one non-nucleic acid analyte on a solid support, said analyte having at least two reporter conjugate binding sites;
(ii) contacting said analyte with at least one reporter conjugate pair, said reporter conjugate pair comprising a first reporter conjugate and a second reporter conjugate, each of said first and second reporter conjugates further comprising:
a) one member of a binding pair having an affinity for at least one reporter conjugate biding site on said analyte;
b) a nucleic acid label;
wherein said nucleic acid label of said first reporter conjugate comprises a 3' hydroxyl group and wherein said nucleic acid label of said second reporter conjugate comprises a 5' phosphoryl group and wherein said analyte binds to said reporter conjugate forming an analyte dependent reporter complex;
(iii) contacting said analyte dependent reporter complex with a DNA ligase,
wherein said first and second nucleic acid labels are ligated to form an analyte specific amplicon;
(iv) contacting said analyte specific amplicon with a replication composition wherein said amplicon is amplified forming amplification products; and
(v) detecting said amplification products.

13. A method according to claim 12 wherein at step (iii) a ligation linker comprising a 3' replication inhibitory moiety is optionally added together with said DNA ligase.

14. A method according to claim 13 wherein said replication inhibitory moiety is selected from the group consisting of dideoxynuleotides, a sequence of mismatched nucleotides, 3' phosphate and cordycepin.

15. A method according to claim 12 wherein said solid support is comprised of materials selected from the group consisting of polyethylene, polypropylene, poly(4-methylbutene), polystyrene, polymethacrylate, poly(ethylene terephthalate), nylon, poly(vinyl butyrate), glass, ceramics, metal and metal oxides.

16. A method according to claim 12 wherein said one member of a binding pair is selected from the group consisting of an antigen, antibody, hapten, nucleic acid, a nucleic acid aptamer, biotin, streptavidin, avidin, folic acid, folate binding protein, protein A protein G, immunoglobulins, epoxide, malaimide and sulfhydryl reactive groups.

17. A method according to claim 12 wherein the at least two reporter conjugates have different specificities for different reporter conjugate binding sites on said analyte.

18. A method according to claim 12 wherein said nucleic acid labels are of different lengths.

19. A method according to claim 12 wherein said nucleic acid labels are of different nucleotide sequence.

20. A method according to claim 12 wherein said nucleic acid labels are from about 25 bases to about 1000 bases in length.

21. A method for the detection of a non-nucleic acid analyte comprising:
(i) contacting at least one non-nucleic acid analyte with at least one reporter conjugate pair, said reporter conjugate pair comprising a first reporter conjugate and a second reporter conjugate, each of said first and second reported conjugates further comprising:
a) one member of a binding pair having an affinity for at least one reporter conjugate biding site on said analyte;
b) a nucleic acid label;
wherein said nucleic acid label of said first reporter conjugate comprises a 3' hydroxyl group and wherein said nucleic acid label of said second reporter conjugate comprises a 5' phosphoryl group and wherein said analyte binds to said reporter conjugate forming an analyte dependent reporter complex;
(ii) contacting said analyte dependent reporter complex with a DNA ligase;
wherein said first and second nucleic acid labels are ligated to form an analyte dependent amplicon;
(iii) contacting said analyte specific amplicon with a replication composition wherein said amplicon is amplified forming amplification products; and
(iv) detecting said amplification products.

22. A method for the detection of a non-nucleic acid analyte comprising:
(i) contacting at least one non-nucleic acid analyte having at least two reporter conjugate binding sites with at least two reporter conjugates, said reporter conjugates each comprising:
   a) one member of a binding pair having specificity for at least one reporter conjugate binding site on said analyte;
   b) a nucleic acid label;
wherein said analyte binds to said reporter conjugates forming an analyte dependent reporter complex;
(ii) contacting said analyte dependent reporter complex with;
   a) an enzyme composition; and
   b) a nucleic acid reporting label selected from the group consisting of fluorescent moieties, chemiluminescent moieties, particles, enzymes, radioactive tags, light emitting moieties and intercalating dyes;
wherein the nucleic acid labels on said reporter conjugates are joined to form an analyte specific amplicon and wherein said nucleic acid reporting label is incorporated into said amplicon; and
(iii) detecting said labeled amplicon.

23. A method according to claim 22 wherein said enzyme composition comprises a DNA polymerase and wherein said nucleic acid labels on said reporter conjugates are joined by an overlap at each 3' end.

24. A method according to claim 22 wherein said enzyme composition comprises a DNA ligase and wherein said nucleic acid labels on said reporter conjugates are enzymatically joined by means of a ligation linker comprising a replication inhibitory moiety.

25. A method according to claim 22 wherein said non-nucleic acid analyte of step (i) is optionally immobilized on a solid support.

26. A method for the detection of a nucleic acid analyte comprising:
(i) contacting at least one nucleic analyte having at least two reporter conjugate binding sites with at least two reporter conjugates, said reporter conjugates each comprising:
   a) one member of a binding pair having specificity for at least one reporter conjugate binding site on said analyte, the one member of a binding pair selected from the group consisting of an antigen, antibody, biotin, streptavidin, avidin, folic acid, folate binding protein, protein A protein G, immunolobulins, epoxide, malaimide and sulfhydryl reactive groups;
   b) a nucleic acid label;
wherein said analyte binds to said reporter conjugates forming an analyte dependent reporter complex;
(ii) contacting said analyte dependent reporter complex with a enzyme composition wherein the nucleic acid labels on said reporter conjugates are joined to form an analyte specific amplicon;
(iii) contacting the analyte specific amplicon with an replication composition wherein amplification products are produced; and
(iv) detecting said amplification products.

* * * * *

(12) EX PARTE REEXAMINATION CERTIFICATE (7689th)
United States Patent
Baez et al.

(10) Number: US 6,511,809 C1
(45) Certificate Issued: Aug. 17, 2010

(54) METHOD FOR THE DETECTION OF AN ANALYTE BY MEANS OF A NUCLEIC ACID REPORTER

(75) Inventors: Luis Baez, West Chester, PA (US); Richard C. Ebersole, Newark, DE (US); Edwin R. Hendrickson, Hockessin, DE (US); Neel Neelkantan, Newark, DE (US); Michael P. Perry, Downington, PA (US)

(73) Assignee: Olink AB, Uppsala (SE)

Reexamination Request:
No. 90/009,222, Jul. 22, 2008

Reexamination Certificate for:
Patent No.: 6,511,809
Issued: Jan. 28, 2003
Appl. No.: 09/858,994
Filed: May 16, 2001

Related U.S. Application Data

(60) Provisional application No. 60/211,293, filed on Jun. 13, 2000.

(51) Int. Cl.
*C12Q 1/68* (2006.01)

(52) U.S. Cl. .............................. 435/6; 435/7.1; 435/91.1; 435/91.2

(58) Field of Classification Search ........................ None
See application file for complete search history.

(56) References Cited

U.S. PATENT DOCUMENTS 5,424,413 A 6/1995 Hogan et al. ............. 536/24.31

FOREIGN PATENT DOCUMENTS

WO WO 97/00446 1/1997

OTHER PUBLICATIONS

Mansfield et al., "Nucleic acid detection using non-radioactive labelling methods," Molecular and Cellular Probes, 9: 149–156, 1995.*
U.S. Appl. No. 60/183,371, filed Feb. 18, 2000, Landegren et al.

* cited by examiner

*Primary Examiner*—Gary L Kunz

(57) ABSTRACT

A process is disclosed for the detection of an analyte utilizing a nucleic acid label as a reporter. The analyte is detected by the binding of at least two reporter conjugates, each conjugate comprising a member of a binding pair and a nucleic acid label. The binding of the reporter conjugates to the analyte facilitates the juxtaposition of the nucleic acid labels, forming a single nucleic acid amplicon. The amplicon may then be detected directly, or may be used as a template of the generation of amplification products. Detection of the analyte by this process significantly reduces assay background caused by non-specific reporter conjugate binding.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 22, 23 and 25 are cancelled.
Claims 1-21, 24 and 26 were not reexamined.
Other new claims 27-43 are cancelled.

\* \* \* \* \*

SEQUENCE LISTING

<160> NUMBER OF SEQ ID NOS: 13

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 1
gcgaggatgg cgaacaacaa ga                                            22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 2

```
accgggggag acgaaactgc t                                                  21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 3
tcgggcggaa tgggtgtggt                                                    20

<210> SEQ ID NO 4
<211> LENGTH: 78
<212> TYPE: DNA
<213> ORGANISM: Artificial Sequence
<220> FEATURE:
<223> OTHER INFORMATION: Description of Artificial Sequence:primer

<400> SEQUENCE: 4
gcgaggatgg cgaacaacaa gactctctct gctttcccat ctatgcgtta attatgatca        60
aactccaggg gccagggc                                                      78

<210> SEQ ID NO 5
<211> LENGTH: 78
<212> TYPE: DNA
<213> ORGANISM: Artificial Sequence
<220> FEATURE:
<223> OTHER INFORMATION: Description of Artificial Sequence:primer

<400> SEQUENCE: 5
gcgaggatgg cgaacaacaa gactctctct gctttcccat ctatgcgtta attatgatca        60
aactccaggg gccagggc                                                      78

<210> SEQ ID NO 6
<211> LENGTH: 68
<212> TYPE: DNA
<213> ORGANISM: Artificial Sequence
<220> FEATURE:
<223> OTHER INFORMATION: Description of Artificial Sequence:primer

<400> SEQUENCE: 6
accgggggag acgaaactgc taacttatat tccttcctac tttgcatcac cacacccatt        60
ccgcccga                                                                 68

<210> SEQ ID NO 7
<211> LENGTH: 68
<212> TYPE: DNA
<213> ORGANISM: Artificial Sequence
<220> FEATURE:
<223> OTHER INFORMATION: Description of Artificial Sequence:primer

<400> SEQUENCE: 7
accgggggag acgaaactgc taacttatat tccttcctac tttgcatcac cacacccatt        60
ccgcccga                                                                 68

<210> SEQ ID NO 8
<211> LENGTH: 68
<212> TYPE: DNA
<213> ORGANISM: Artificial Sequence
<220> FEATURE:
<223> OTHER INFORMATION: Description of Artificial Sequence:primer
```

-continued

```
<400> SEQUENCE: 8 accggggag acgaaactgc taacttatat tccttcctac tttgcatcac cacacccatt      60
ccgcccga                                                              68

<210> SEQ ID NO 9
<211> LENGTH: 68
<212> TYPE: DNA
<213> ORGANISM: Artificial Sequence
<220> FEATURE:
<223> OTHER INFORMATION: Description of Artificial Sequence:primer

<400> SEQUENCE: 9 accggggag acgaaactgc taacttatat tccttcctac tttgcatcac cacacccatt      60
ccgcccga                                                              68

<210> SEQ ID NO 10
<211> LENGTH: 66
<212> TYPE: DNA
<213> ORGANISM: Artificial Sequence
<220> FEATURE:
<223> OTHER INFORMATION: Description of Artificial Sequence:primer

<400> SEQUENCE: 10
gcgaggatgg cgaacaacaa gactctctct gctttccaat ctatgcgtta attatgatct      60
cgggcg                                                                66

<210> SEQ ID NO 11
<211> LENGTH: 66
<212> TYPE: DNA
<213> ORGANISM: Artificial Sequence
<220> FEATURE:
<223> OTHER INFORMATION: Description of Artificial Sequence:primer

<400> SEQUENCE: 11
gcgaggatgg cgaacaacaa gactctctct gctttccaat ctatgcgtta attatgatct      60
cgggcg                                                                66

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence:primer

<400> SEQUENCE: 12
agcagtttcg tctcccccgg tgccctcgcc cctggagttt g                         41

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 13
ttcgtctccc ccggtgccct cgcccctgg                                       29
```